US011292759B2

(12) United States Patent
Clouatre et al.

(10) Patent No.: US 11,292,759 B2
(45) Date of Patent: Apr. 5, 2022

(54) HYDROXYCITRIC ACID METAL HETEROCYCLIC COMPOUNDS WITH COVALENT CHARACTERISTICS

(71) Applicant: GLYKON TECHNOLOGIES GROUP, LLC, Seattle, WA (US)

(72) Inventors: Daniel E. Clouatre, Seattle, WA (US); Nimpan Bangun, Seattle, WA (US); Dallas L. Clouatre, Seattle, WA (US)

(73) Assignee: Nutrition Research Group, Limited, London (GB)

(*) Notice: Subject to any disclaimer, the term of this patent is extended or adjusted under 35 U.S.C. 154(b) by 0 days.

(21) Appl. No.: 16/970,794

(22) PCT Filed: Mar. 1, 2019

(86) PCT No.: PCT/US2019/020329
§ 371 (c)(1),
(2) Date: Aug. 18, 2020

(87) PCT Pub. No.: WO2019/173150
PCT Pub. Date: Sep. 12, 2019

(65) Prior Publication Data
US 2021/0107855 A1 Apr. 15, 2021

Related U.S. Application Data

(60) Provisional application No. 62/639,728, filed on Mar. 7, 2018.

(51) Int. Cl.
C07C 59/265 (2006.01)
C07F 13/00 (2006.01)
A61K 31/194 (2006.01)
C07F 1/00 (2006.01)
C07F 3/06 (2006.01)
C07F 3/02 (2006.01)
C07F 3/04 (2006.01)
A61P 3/00 (2006.01)
A61P 19/02 (2006.01)
A61P 29/00 (2006.01)
A61P 19/10 (2006.01)

(52) U.S. Cl.
CPC .......... C07C 59/265 (2013.01); A61K 31/194 (2013.01); C07F 1/005 (2013.01); C07F 3/02 (2013.01); C07F 3/04 (2013.01); C07F 3/06 (2013.01); C07F 13/005 (2013.01); A61P 3/00 (2018.01); A61P 19/02 (2018.01); A61P 19/10 (2018.01); A61P 29/00 (2018.01)

(58) Field of Classification Search
CPC ... C07C 59/265; C07C 59/285; C07C 51/412; A61K 31/194; C07F 3/02; C07F 3/04; C07F 3/06; C07F 3/003; C07F 132/005
See application file for complete search history.

(56) References Cited

U.S. PATENT DOCUMENTS

| | | | | |
|---|---|---|---|---|
| 5,679,344 A * | 10/1997 | Williams | ........... | A61K 38/4826 424/94.63 |
| 6,160,172 A * | 12/2000 | Balasubramanyam | ...................... | C07C 51/412 562/584 |
| 7,208,615 B2 * | 4/2007 | Gokaraju | .............. | C07C 51/412 424/439 |
| 7,741,370 B2 * | 6/2010 | Gokaraju | .................. | A61P 3/04 514/574 |
| 2004/0259937 A1 * | 12/2004 | Samuel | .................. | A61K 36/82 514/460 |
| 2010/0152488 A1 * | 6/2010 | Rao | ........................ | C07C 59/245 562/584 |
| 2013/0150448 A1 * | 6/2013 | Moffett | ..................... | A61P 3/04 514/574 |

FOREIGN PATENT DOCUMENTS

| | | | | |
|---|---|---|---|---|
| EP | 0 866 137 A1 * | 9/1998 | ........... | C07C 59/245 |
| JP | 2014218422 A * | 11/2014 | ............. | C07C 67/10 |
| WO | WO-2004100682 A1 * | 11/2004 | ............. | A61K 36/82 |
| WO | WO 2005/099679 A1 | 10/2005 | | |

(Continued)

OTHER PUBLICATIONS

JP2014218442 A, Kobayashi et al., Method for Benzylating hydroxy tricarboxylic acid, English translation, 10 pages (Year: 2014).*
Rao, G.V., et al., Hydroxycitric acid lactone and its salts: Preparation and appetite suppression studies, Food Chemistry, 120(1), pp. 235-239 (Year: 2010).*

(Continued)

Primary Examiner — Yate' K Cutliff
(74) Attorney, Agent, or Firm — Karl Bozicevic; Bozicevic, Field & Francis LLP

(57) ABSTRACT

Hydroxycitric acid-metal heterocyclic compounds with covalent characteristics are provided. The subject hydroxycitric acid compounds include monomeric hydroxycitric acid (HCA) compounds having a divalent metal, lactone forms thereof, and dimeric compound forms thereof. The monomeric HCA compound includes a divalent metal (X) bonded via a 5-membered ring to both the carboxylic acid and the hydroxy group of the central C2 carbon of the HCA. In addition, a monovalent metal (Y) can also be bonded to the carboxylic acid of C3 or C1, or to both C1 and C3. The subject dimeric compounds include monomeric HCA compounds linked via a second divalent metal (X) to a carboxylic acid group of each HCA unit at C3 or C1. Also provided are compositions including a monomeric HCA compound and one or more other additional compounds. Methods of alleviating at least one symptom associated with a target disease or condition in a subject are provided.

10 Claims, No Drawings

(56) References Cited

FOREIGN PATENT DOCUMENTS

| WO | WO 2007/010838 A1 | 1/2007 |
|----|-------------------|--------|
| WO | WO 2008/099413 A2 | 8/2008 |
| WO | WO 2011/051899 A1 | 5/2011 |
| WO | WO 2018/049216 A1 | 3/2018 |
| WO | WO 2018/080795 A1 | 5/2018 |

OTHER PUBLICATIONS

National Center for Biotechnology Information (2021). PubChem Compound Summary for CID 10130001, Zinc;2-oxidoacetate. Retrieved Oct. 19, 2021 from https://pubchem.ncbi.nlm.nih.gov/compound/10130001, created Oct. 25, 2006, 8 pages (Year: 2006).*

National Center for Biotechnology Information (2021). PubChem Compound Summary for CID 129701542, Malate oxaloacetate manganese. Retrieved Oct. 20, 2021 from https://pubchem.ncbi.nlm.nih.gov/compound/Malate-oxaloacetate-manganese, created Sep. 13, 2017, 8 pages (Year: 2017).*

Venkhateswara Rao G, et al. "Hydroxycitric acid lactone and its salts: Preparation and appetite suppression studies", Food Chemistry, Elsevier Ltd, NL, vol. 120, No. 1, May 1, 2020, pp. 235-239.

\* cited by examiner

HYDROXYCITRIC ACID METAL HETEROCYCLIC COMPOUNDS WITH COVALENT CHARACTERISTICS

INTRODUCTION

Hydroxycitric acid (HCA) is a derivative of citric acid found in the fruit of members of the plant genus *Garcinia*. There are four isomers of, (+)- and (−)-hydroxycitric acid, and (+) - and (−)-allo-hydroxycitric acid. The (−)-hydroxycitric acid isomer is the one found in *Garcinia* (see e.g., Jena et al. "Chemistry and Biochemistry of (−)-Hydroxycitric Acid from *Garcinia*." Journal of Agricultural and Food Chemistry 50(1):10-22). Free HCA can be present in solution in an acid form and/or a lactone form. Calcium, magnesium and potassium salts of HCA are described, e.g., in U.S. Pat. Nos. 8,394,856 and 7,943,186. Compositions including calcium HCA and sodium HCA salts have been sold commercially since 1994.

(−)-HCA is a potent inhibitor of ATP citrate lyase (EC 4.1.3.8), which catalyzes the extramitochondrial cleavage of citrate to oxaloacetate and acetyl-CoA. The inhibition of this reaction limits the availability of acetyl-CoA units required for fatty acid synthesis and lipogenesis during a lipogenic diet. HCA can have several biological effects (Jena et al. "Chemistry and Biochemistry of (−)-Hydroxycitric Acid from *Garcinia*" J. Agric. Food Chem., 2002, 50 (1), pp 10-22). HCA can affect the metabolic and other physiologic functions of mammals, including humans. HCA, as well as several synthetic derivatives of citric acid, can inhibit the production of fatty acids from carbohydrates, suppress appetite and inhibit weight gain (Sullivan et al., American Journal of Clinical Nutrition 1977; 30: 767). Numerous other benefits have been attributed to the use of HCA, including, but not limited to, an increase in the metabolism of fat stores for energy and an increase in thermogenesis, and wound healing.

A number of different HCA salt forms and compositions have been investigated. Potassium HCA and sodium HCA salt forms are extremely hygroscopic. The therapeutic use of HCA salts is limited by poor absorption and chemical instability at acidic pH, e.g., inactivation of HCA salts via lactonization upon exposure to the acidic milieu of prepared drinks and the mammalian gut. Some calcium salts of HCA exhibit especially poor bioavailability. Particular double and triple-metal salt compositions prepared using conventional methods exhibit similarly poor bioavailability despite improved solubility. For example, a peak blood plasma HCA concentration was reached in subjects approximately 2 hours after administration of Super Citrimax potassium/calcium (−)-hydroxycitrate, indicating only partial absorption of HCA by the subjects. See also, Anal. Biochem., 2001 May 1; 292(1): 148-54; and FASEB Journal 15; 4:632, Abs. 501.1, 2001, 38.

Dosages of various HCA compositions found to be effective are quite large, indeed beyond the normal range for pharmaceutical products, with efficacy that is highly variable. The effective dose at which HCA is found to significantly decrease de novo lipogenesis (DNL) in rats is 1.32 mmol/kg/day or 0.27 g/kg/day (Lipids. 1974 February; 9(2):121-8) This extrapolates to approximately 4.5 g/day for a 70 kg human being. One study with obese subjects indicated that administering 6 g HCA/day for 5 days failed to inhibit DNL or to promote fatty acid oxidation Anal Biochem. 2001 May 1; 292(1):148-54). A later study found a significant, yet limited effect after 7 days of a diet designed specifically to induce de novo lipogenesis in humans. (Physiol Behav. 2006 Jul. 30; 88(4-5): 371-81). See also, Nutr Metab (Lond). 2005 Sep. 13; 2:23. Experimental work with animals has demonstrated considerable differences in both efficacy and modes of action among the various conventional HCA salt forms.

SUMMARY

Hydroxycitric acid-metal heterocyclic compounds with covalent characteristics are provided. The subject hydroxycitric acid compounds include monomeric hydroxycitric acid (HCA) compounds having a divalent metal, lactone forms thereof, and dimeric compound forms thereof. The monomeric HCA compound includes a divalent metal (X) bonded via a 5-membered ring to both the carboxylic acid and the hydroxy group of the central C2 carbon of the HCA. In addition, a monovalent metal (Y) can also be bonded to the carboxylic acid of C3 or C1, or to both C1 and C3. The subject dimeric compounds include two of the monomeric HCA compounds linked via a second divalent metal (X) which can connect to a carboxylic acid group of each HCA unit at C3 or C1. Also provided are compositions including a monomeric HCA compound and one or more other additional monomeric or dimeric HCA compounds. Methods of alleviating at least one symptom associated with a target disease or condition in a subject are provided. Also provided are pharmaceutical or nutraceutical ingredients and compositions including the subject monomeric and dimeric HCA compounds which find use in a variety of therapeutic applications.

DEFINITIONS

Before describing exemplary embodiments in greater detail, the following definitions are set forth to illustrate and define the meaning and scope of the terms used in the description. Any undefined terms have their art recognized meanings.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

As used herein, the terms "metal HCA" and "HCA metal compound" are used interchangeably to refer to the subject compounds and compositions that include HCA and a divalent metal atom bonded to the HCA. In some cases, the compound is a bimetal compound including two metal atoms and an HCA molecule, where the two metal atoms can be considered two distinct and different metal ions (e.g., a first divalent metal and a second monovalent metal) that form individual bonds to groups of the HCA molecules that can have significant covalent character. The ratio of HCA to the two metal atoms can be 1:1:1. In some cases, the compound is a trimetal compound including three metal atoms and an HCA molecule, where the three metal atoms can be considered distinct and different metal ions (e.g., a first divalent metal and two additional monovalent metals).

It is understood, unless otherwise stated, that as used herein, references to groups of the periodic table correspond to the old IUPAC European system.

A heterocyclic compound or ring structure is a cyclic compound or structure that has atoms of at least two different elements as members of its ring(s), e.g., a carbon atom and at least one non-carbon atom selected from a N, O or S atom, or a metal atom.

The terms divalent and bivalent refer to an atom, metal, ion, functional group, or molecule that has a valence of two. Valency is the number of chemical bonds formed, which may be covalent or ionic.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

Bioavailability is a subcategory of absorption and is the fraction of an administered dose of unchanged drug that reaches the systemic circulation. The terms absorption and uptake refer to the process of transport of a compound from the intestinal or gut lumen into the systemic circulation.

Also of interest as active agents for use in embodiments of the methods are prodrugs. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the methods and compositions of the present disclosure. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, succinates, and ethylsuccinates.

Other definitions of terms may appear throughout the specification.

DETAILED DESCRIPTION

Before the present compounds, formulations, methods of preparation and uses are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the reaction" includes reference to one or more reactions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

HCA Monomeric Compounds

Aspects of the present disclosure include monomeric compounds of hydroxycitric acid (HCA), and/or lactone forms thereof, that include at least one metal, e.g., a first divalent metal ion and in some cases at least one monovalent metal ion. In some instances, the compound is a metal heterocyclic compound of HCA exhibiting covalent characteristics, e.g., where the bonds between a divalent metal ion and the HCA exhibit covalent characteristics. In some cases, the HCA compound is present in combination with a monomeric HCA lactone compound (i.e. wherein the HCA compounds and lactone forms thereof are in an equilibrium mixture). Aspects of the present disclosure also include dimeric hydroxycitric acid (HCA) metal compounds exhibiting covalent characteristics. In some cases, the dimeric HCA compound is present in combination with monomeric HCA compounds and lactone forms thereof. The subject HCA-derived compounds, methods of synthesis, as well as examples of their physiologic uses along with showings of in vivo activity are disclosed and described herein.

The structures and physical and chemical properties of the subject monomeric HCA compounds and lactones thereof differ from those of known HCA compounds, HCA salts and mixtures of HCA salts, even those that include similar metal ions, proportions of the HCA and metals, as well as similar pH conditions. In some cases, the conventional HCA salts form multimeric structures. HCA includes three saturated carbon atoms (C1-C3), each substituted with a carboxylic acid (—CO$_2$H), and where C1 and C2 are further substituted with hydroxy groups. The C1 carboxylic acid has a more acidic pKa as compared to the C3 carboxylic acid group (acetic acid pKa approx. 4.76 versus glycolic acid pKa approx. 3.83).

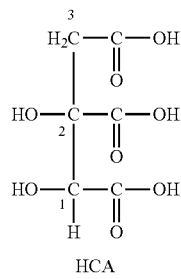

HCA

HCA isomers of interest from which the subject monomeric HCA compounds and dimeric HCA compounds can be derived include, but are not limited to, (+)-hydroxycitric acid, (−)-hydroxycitric acid, (+)-allo-hydroxycitric acid and (−)-allo-hydroxycitric acid. In certain embodiments, the compound is derived from (−)-hydroxycitric acid.

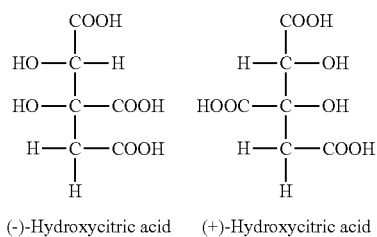

(−)-Hydroxycitric acid     (+)-Hydroxycitric acid

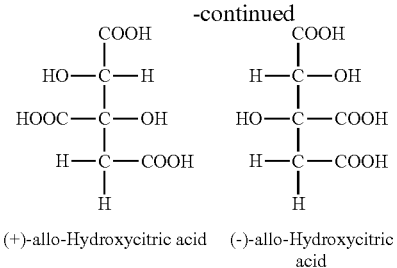

(+)-allo-Hydroxycitric acid     (−)-allo-Hydroxycitric acid

In conventional HCA preparations, HCA and salts thereof can convert to a lactone form and/or be present in an equilibrium with the lactone form. Lactone forms of HCA include the following:

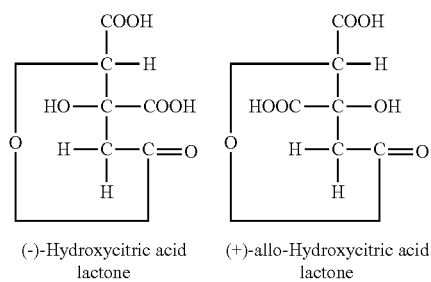

(−)-Hydroxycitric acid lactone     (+)-allo-Hydroxycitric acid lactone

As summarized above, in the subject HCA-metal compound, a divalent metal (X) is bonded via a 5-membered ring to both the carboxylic acid and the hydroxy group of the central C2 carbon of the HCA. As such, the C1 hydroxy group can be available to form an intramolecular lactone with, e.g, the C3 carboxylic acid group, under certain conditions. The subject methods and compounds provide for monomeric forms of HCA, and lactone forms thereof, that include a divalent metal (X) bonded to the carboxylic acid and the hydroxy group of C2 via a 5-membered ring, and a monovalent metal (Y) bonded to the carboxylic acid of C1 and/or C3, depending on whether the lactone ring is present. The subject methods of preparation provide for selective installation of a first divalent metal and a second monovalent metal into HCA with a particular configuration of metal-HCA bonds to produce a monomeric bimetal HCA compound with covalent characteristics. The subject methods of preparation provide for preparation of monomeric compounds, e.g., a compound including one and only one molecule of HCA per first and second metal, without formation of an undesirable mixture of dimeric and/or oligomeric HCA forms. The subject methods can also provide for preparation of monomeric HCA compounds without formation of significant amounts of dimeric and/or oligomeric HCA compounds. In other embodiments, the subject HCA compound is present in combination with monomeric HCA lactone compounds (i.e. wherein the HCA compounds and HCA lactone compounds are in an equilibrium mixture).

As summarized above, the first divalent metal (X) bonds to the carboxylic acid group and the hydroxy group of C2 of the HCA molecule to form the 5-membered heterocyclic ring of the subject compound. The O—X—O bonds of the 5-membered heterocyclic ring can be characterized as having covalent character. In some embodiments, the O—X—O bonds of the 5-membered heterocyclic ring can be characterized as having substantial covalent character. By "substantial covalent character" is meant 50% or more covalent character, such as 60% or more, 70% or more, 80% or more, 90% or more, or 95% or more covalent character, as determined by any convenient method, e.g., via conductivity of an aqueous solution of the compound relative to a control, e.g., as described in the experimental section.

In addition, a monovalent metal ion (Y) may be installed into the compound via bonding to the C3 or C1 carboxylic acid group. In some cases, the 5-membered heterocyclic ring is substantially stable in an aqueous environment, such that the first divalent metal (X) does not substantially dissociate from the HCA compound. In certain instances, the second monovalent metal (Y) has covalent character and does not fully dissociate from the HCA compound in an aqueous solution. It is understood that the bonding of the first and/or second metals to the hydroxycitric acid can be referred to as the result of bonding of carboxylate group(s) and hydroxy group(s) of HCA and first and second metal ions, where the bonds that are formed can be characterized as having a particular covalent character and/or a particular ionic character. In some cases, the first metal is a divalent metal that forms polar covalent bonds to the HCA compound. In certain cases, the second metal is a monovalent metal that forms a bond with the HCA compound that has partial covalent character and partial ionic character, e.g., such that the second monovalent metal can at least partially dissociate from the HCA compound under suitable aqueous conditions.

The subject monomeric HCA compound can be described by formula (I):

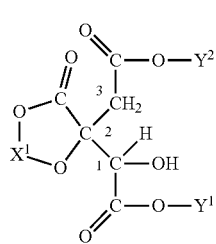

(I)

wherein $X^1$ is a divalent metal, $Y^1$ is hydrogen or a monovalent metal and $Y^2$ is hydrogen or a monovalent metal, or a lactone form thereof. In certain cases, the HCA compound of formula (I) is a hydrated form thereof. $X^1$ can be a divalent metal selected from Group IIA metals, Group IIB metals and Group VIIA metals. In certain cases $Y^2$ is hydrogen. In other cases, $Y^2$ is a monovalent metal. In certain cases $Y^1$ is hydrogen. In a lactone form of formula (I), the —$OY^2$ is absent and the hydroxyl of C1 is cyclically linked to the C3 carbonyl group to provide a lactone ring in the compound.

In some embodiments of the HCA compound of formula (I), $X^1$ is selected from Mg, Ca, Sr, Zn and Mn; and $Y^1$ and $Y^2$ are independently selected from H, Li, Na and K. In certain embodiments of a compound of formula (I), $Y^1$ and $Y^2$ are Li. In other cases, $Y^1$ and $Y^2$ are both Na. In certain other cases, $Y^1$ and $Y^2$ are both K. In some embodiments of a compound of formula (I), $X^1$ is Mg. In other cases, $X^1$ is Ca. In some other cases, $X^1$ is Sr. In certain other cases, $X^1$ is Zn. In some instances, $X^1$ is Mn. In certain other cases $Y^1$ is a monovalent metal. In some embodiments, both $Y^1$ and $Y^2$ are hydrogen.

In certain cases, the HCA compound of formula (I) is a bimetal compound selected from formula (IA) or (IB):

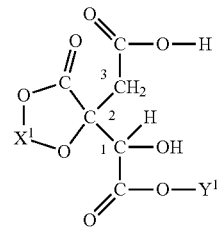

(IA)

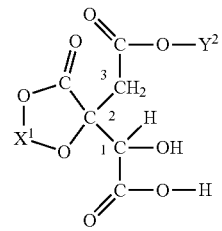

(IB)

wherein $X^1$ is a divalent metal selected from Group IIA metals, Group IIB metals and Group VIIA metals, and $Y^1$ and $Y^2$ are each independently selected from a monovalent metal, e.g. Li, Na and K.

In certain embodiments, the HCA compound of formula (I) is the lactone of formula (II):

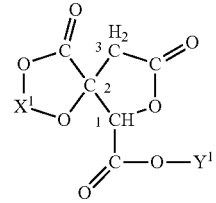

(II)

wherein $X^1$ is a divalent metal selected from Group IIA metals, Group IIB metals and Group VIIA metals, and $Y^1$ is hydrogen or a monovalent metal.

In certain instances, when a subject compound is contacted with a suitable aqueous solution, the monomeric metal can dissociate from the subject monomeric bimetal compound and become hydrated to result in an ionic binary complex, e.g., as follows for a compound of formula (I):

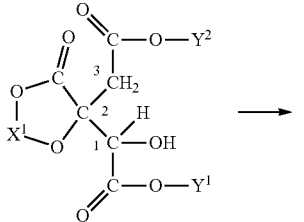

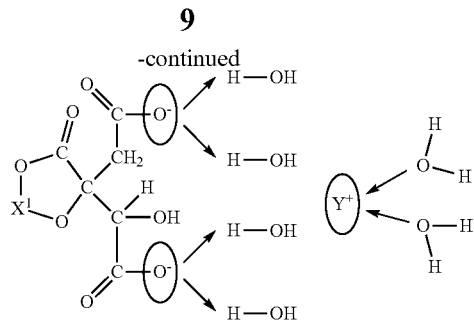

It is understood that in the depictions of compound structures herein, any carboxylate groups can be present as a carboxylic acid and/or in a hydrated form.

In certain embodiments, when the subject compound is contacted with an aqueous solution, no significant dissociation of the first and/or second metal from the compound occurs.

In some cases, when a compound of formula (II) is contacted with an aqueous solution, the lactone compound is converted into a combination of monomeric HCA bimetal compounds, including, but not limited to compounds of formulas (IA) and (IB), or a hydrate thereof. In some cases when a compound of formula (II) is contacted with an aqueous solution, the lactone compound is slowly converted to monomeric HCA bimetal compounds, to result in an equilibrium mixture of a lactone compound of formula (II) and monomeric HCA compounds (e.g. of formulae (IA) and (IB)). In certain cases, the equilibrium contains about a 1:1 mixture of monomeric HCA compounds to lactone compounds. In other cases, the equilibrium contains a greater concentration of monomeric HCA compounds than lactone compounds, such that a 1.1:1, 1.2:1, 1.3:1, 1.4:1, 1.5:1, 1.6:1, 1.7:1, 1.8:1, 1.9:1 or a 2:1 mixture of monomeric HCA compounds to lactone compounds is present in the equilibrium mixture. In certain cases, the equilibrium contains about a 1.5:1 mixture of monomeric HCA compounds to lactone compounds. In other cases the equilibrium contains a lesser concentration of monomeric HCA compounds than lactone compounds, such that a 1:1.1, 1:1.2, 1:1.3, 1:1.4, 1:1.5, 1:1.6, 1:1.7, 1:1.8, 1:1.9 or 1:2 mixture of monomeric HCA compounds to lactone compounds is present in the equilibrium mixture. In certain cases, the equilibrium contains about a 1:1.5 mixture of monomeric HCA compounds to lactone compounds.

In some embodiments of an HCA compound of formula (I) or (II), $X^1$ is a Group IIA group metal. In some cases, $X^1$ is selected from Mg, Ca, Sr, Ba and Ra. In some cases $X^1$ is Mg. In some cases $X^1$ is Ca. In other cases $X^1$ is Sr. In other cases $X^1$ is Ba. In some other cases $X^1$ is Ra.

In some embodiments of an HCA compound of formula (I) or (II), $X^1$ is a Group IIB group metal. In certain cases, $X^1$ is Zn.

In some embodiments of an HCA compound of formula (I) or (II), $X^1$ is a Group VIIA group metal. In some cases, $X^1$ is Mn.

In some embodiments of an HCA compound of formula (I) or (II), $Y^1$ and $Y^2$ are each independently a Group IA metal. In some cases, the Group IA metal is selected from Li, Na and K. In certain cases, the Group IA metal is K.

In some embodiments of an HCA compound of formula (I) or (II), at least one of $Y^1$ and $Y^2$ is H.

In certain embodiments of an HCA compound of formula (I) or (II), the HCA is (−)-hydroxycitric acid. Monomeric compounds of interest include those described in Tables 1-3.

TABLE 1

Compounds of interest of Formula (I)

| Compound of Formula (I) | $X^1$ | $Y^1$ and $Y^2$ |
| --- | --- | --- |
| 1 (Li$_2$MgHCA) | Mg | Li |
| 2 (Li$_2$CaHCA) | Ca | Li |
| 3 (Li$_2$SrHCA) | Sr | Li |
| 4 (Li$_2$ZnHCA) | Zn | Li |
| 5 (Li$_2$MnHCA) | Mn | Li |
| 6 (Na$_2$MgHCA) | Mg | Na |
| 7 (Na$_2$CaHCA) | Ca | Na |
| 8 (Na$_2$SrHCA) | Sr | Na |
| 9 (Na$_2$ZnHCA) | Zn | Na |
| 10 (Na$_2$MnHCA) | Mn | Na |
| 11 (K$_2$MgHCA) | Mg | K |
| 12 (K$_2$CaHCA) | Ca | K |
| 13 (K$_2$SrHCA) | Sr | K |
| 14 (K$_2$ZnHCA) | Zn | K |
| 15 (K$_2$MnHCA) | Mn | K |

TABLE 2

Compounds of interest of Formula (IA)

| Compound of Formula (IA) | $X^1$ | $Y^1$ |
| --- | --- | --- |
| 1 (LiMgHCA) | Mg | Li |
| 2 (LiCaHCA) | Ca | Li |
| 3 (LiSrHCA) | Sr | Li |
| 4 (LiZnHCA) | Zn | Li |
| 5 (LiMnHCA) | Mn | Li |
| 6 (NaMgHCA) | Mg | Na |
| 7 (NaCaHCA) | Ca | Na |
| 8 (NaSrHCA) | Sr | Na |
| 9 (NaZnHCA) | Zn | Na |
| 10 (NaMnHCA) | Mn | Na |
| 11 (KMgHCA) | Mg | K |
| 12 (KCaHCA) | Ca | K |
| 13 (KSrHCA) | Sr | K |
| 14 (KZnHCA) | Zn | K |
| 15 (KMnHCA) | Mn | K |

TABLE 3

Compounds of interest of Formula (IB)

| Compound of Formula (IB) | $X^1$ | $Y^2$ |
| --- | --- | --- |
| 1 (LiMgHCA) | Mg | Li |
| 2 (LiCaHCA) | Ca | Li |
| 3 (LiSrHCA) | Sr | Li |
| 4 (LiZnHCA) | Zn | Li |
| 5 (LiMnHCA) | Mn | Li |
| 6 (NaMgHCA) | Mg | Na |
| 7 (NaCaHCA) | Ca | Na |
| 8 (NaSrHCA) | Sr | Na |
| 9 (NaZnHCA) | Zn | Na |
| 10 (NaMnHCA) | Mn | Na |
| 11 (KMgHCA) | Mg | K |
| 12 (KCaHCA) | Ca | K |
| 13 (KSrHCA) | Sr | K |
| 14 (KZnHCA) | Zn | K |
| 15 (KMnHCA) | Mn | K |

Any convenient divalent metals (X) can be utilized in the subject compounds. In some embodiments of any of formulas (I)-(VI), X (e.g. as in $X^1$ or $X^2$) is a metal selected from Group IIA metals, Group IIB metals and Group VIIA metals. It is understood, unless otherwise stated, that as used herein, references to groups of the periodic table correspond to the old IUPAC European system.

X can be a Group IIA metal. Group IIA metals of interest include, beryllium (Be), magnesium (Mg), calcium (Ca), strontium (Sr), barium (Ba) and radium (Ra). In certain instances of any of formulas (I)-(VI) X (e.g. as in $X^1$ or $X^2$) is selected from Mg, Ca, Sr, Ba and Ra. In certain cases of any of formulas (I)-(VI), X is Mg. In certain cases of any of formulas (I)-(VI), X is Ca. In certain cases of any of formulas (I)-(VI), X is Sr. In certain cases of any of formulas (I)-(VI), X is Ba. In certain cases of any of formulas (I)-(VI), X is Ra.

X can be a Group IIB metal. Group IIB metals of interest include, but are not limited to, zinc (Zn) and cadmium (Cd). In certain cases of any of formulas (I)-(VI), X is Zn. In certain cases of any of formulas (I)-(VI), X is Cd.

X can be a Group VIIA metal. Group VIIA metals of interest include, manganese (Mn), technetium (Tc), rhenium (Re) and bohrium (Bh). In certain cases of any of formulas (I)-(VI), X is Mn. In certain cases of any of formulas (I)-(VI), X is Tc. In certain cases of any of formulas (I)-(VI), X is Re. In certain cases of any of formulas (I)-(VI), X is Bh.

Any convenient monovalent metals (Y) can be utilized in the subject compounds. In some embodiments of any of formulas (I)-(VI), Y (e.g. as in any of $Y^1$-$Y^4$) is a Group IA metal. Group IA metals of interest include, lithium (Li), sodium (Na), potassium (K), rubidium (Rb) and cesium (Cs). In certain cases of any of formulas (I)-(VI), any of $Y^1$-$Y^4$ are independently Li, Na or K. In certain cases of any of formulas (I)-(VI), any of $Y^1$-$Y^4$ are Li. In certain cases of any of formulas (I)-(VI), any of $Y^1$-$Y^4$ are Na. In certain cases of any of formulas (I)-(VI), any of $Y^1$-$Y^4$ are K.

In some embodiments of any of formulas (I)-(VI), X (as in $X^1$ or $X^2$) is selected from Mg, Ca, Sr, Zn and Mn and any of $Y^1$-$Y^4$ are independently selected from Li, Na and K. In some embodiments of any of formulas (I)-(VI) X is selected from Mg, Ca, Sr, Zn and Mn and any of $Y^1$-$Y^4$ are Li. In some embodiments of any of formulas (I)-(VI), X is selected from Mg, Ca, Sr, Zn and Mn and any of $Y^1$-$Y^4$ is Na. In some embodiments of any of formulas (I)-(VI), X is selected from Mg, Ca, Sr, Zn and Mn and any of $Y^1$-$Y^4$ are K.

In certain instances, the subject monomeric HCA compound of formula (I) is a compound of formula (IA) as shown in Table 1. In certain embodiments, the HCA compound as disclosed herein in Table 1 is in its lactone form e.g. a compound of formula (II). In certain instances, the subject monomeric HCA compound of formula (I) is a compound of formula (IB) as shown in Table 2. In certain instances, the subject monomeric HCA compound of formula (I) is a compound as shown in Table 3, wherein both $Y^1$ and $Y^2$ are monomeric metals. In certain instances of any one of the embodiments described herein (e.g., a compound of Table 1-3), the HCA is (−)-hydroxycitric acid.

In some embodiments, X is Ca and Mg, e.g., referred as KCaHCA.3H$_2$O and KMgHCA.8H$_2$O. Group IIA metals of interest include Be, Mg, Ca, Sr, Ba and Ra, e.g., having ionic radii of Be$^{2+}$(0.31 A°), Mg (0.65 A°) and Ca$^{2+}$(0.92 A°). Because of small radii of Be$^2$±, Be(OH)$_2$ has very high covalent character therefore it is sparingly soluble in water. Similarly, Mg(OH)$_2$ has very low solubility in water because Mg$^{2+}$ has small ionic radii and therefore bonding Mg—O has high covalent character.

The subject monomeric compounds can provide for desirable uptake or absorption by a subject. In some cases, the monomeric compounds provide for a desirable bioavailability, e.g., as compared to conventional salt forms of HCA that may be dimeric or oligomeric. In some cases, the subject monomeric HCA compounds and lactones thereof provide for enhanced bioavailability, e.g., as compared to conventional salt forms of HCA that may be dimeric or oligomeric and other known monomeric HCA compounds. In some instances the bioavailability of the subject monomeric HCA compounds is at least 2-fold greater than that of conventional salt forms of HCA (e.g. monomeric, dimeric or oligomeric) and other known monomeric HCA compounds and dimeric HCA compounds. In some instances, the bioavailability of the subject HCA compounds is greater than 2-fold more than other known HCA compounds, such as 3-fold, 4-fold, 5-fold, 6-fold, 7-fold, 8-fold, 9-fold or 10-fold greater, or even greater than a known HCA compound. In some instances the bioavailability of the subject HCA compounds is 10-fold or greater than other known HCA compounds.

In some instances, exemplary monomeric HCA compound of formula (IA) or its lactone form thereof (e.g. of formula (II)), KMgHCA when contacted with a suitable aqueous solution, can dissociate into, e.g., K$^+$ and [MgHCA]$^−$. In certain cases, MgHCA$^−$ can be easily transported into a cell as a small ionic species with a small electric charge. In certain instances, a mixture of KMgHCA and KCaHCA compounds of formula (IA) of formula (II) may provide increased solubility of the compounds in water. In certain instances, such compounds and mixtures of compounds can form an intermediate (e.g., in situ) including but not limited to penta metal HCA compound (A), a trimetal HCA compound (B) or a coordinating OH ligand (C), as shown below.

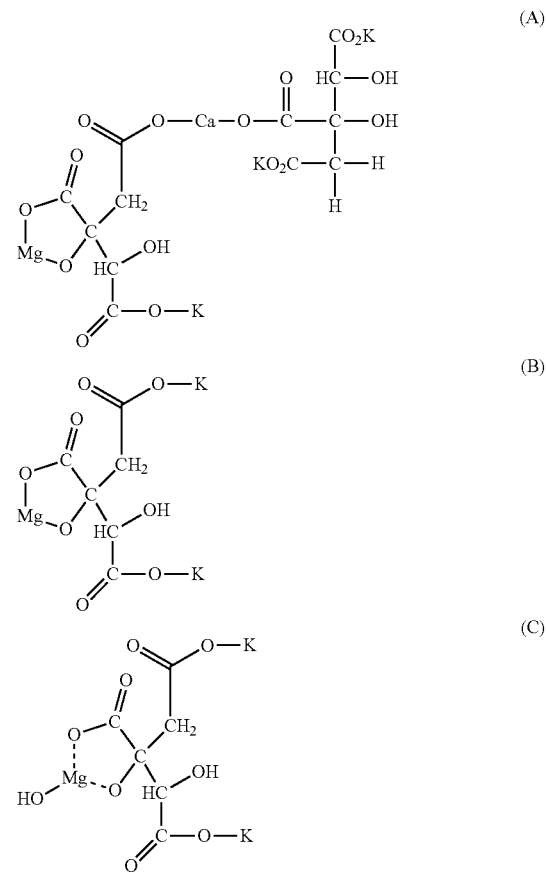

HCA Dimeric Compounds

Dimeric forms of any of the monomeric compounds described herein can also find use in the subject compounds. In general terms, a dimeric form of a monomeric compound may be provided by installing a second divalent metal in place of an existing monomeric metal (e.g., $Y^1$ or $Y^2$) to allow for dimerization of a HCA molecule. In such cases, the first divalent metal (e.g., $X^1$) remains in place as part of the heterocyclic ring of interest. Both homodimeric and heterodimeric versions monomeric HCA compounds of interest are included in this disclosure.

In some embodiments, dimeric hydroxycitric acid (HCA) metal compounds of formula (VII) are provided:

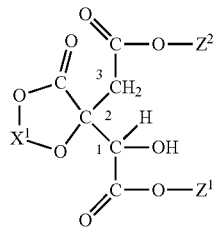
(VII)

wherein, $X^1$ is a divalent metal selected from Group IIA metals, Group IIB metals and Group VIIA metals, one of $Z^1$ and $Z^2$ is a divalent metal bonded to a second hydroxycitric acid compound (HCA) and the other of $Z^1$ and $Z^2$ is hydrogen or a monovalent metal.

In certain cases of a compound of formula (VII), $Z^1$ is a divalent metal bonded to a second HCA compound and $Z^2$ is a monovalent metal. In other cases of a compound of formula (VII), $Z^2$ is a divalent metal bonded to a second HCA compound and $Z^1$ is a monovalent metal. In some cases of a compound of formula (VII), $Z^1$ is a divalent metal bonded to a second HCA compound and $Z^2$ is hydrogen. In other cases of a compound of formula (VII), $Z^2$ is a divalent metal bonded to a second HCA compound and $Z^1$ is hydrogen. In certain embodiments a compound of formula (VII) is present in a hydrated form.

In some embodiments of a dimeric HCA compound of formula (VII), $X^1$ is selected from Mg, Ca, Sr, Zn and Mn; and one of $Z^1$ and $Z^2$ is selected from H, Li, Na and K. In certain embodiments of a compound of formula (VII), one of $Z^1$ or $Z^2$ is Li. In other cases, one of $Z^1$ or $Z^2$ is Na. In certain other cases, one of $Z^1$ or $Z^2$ is K. In some embodiments of a compound of formula (VII), $X^1$ is Mg. In other cases, $X^1$ is Ca. In some other cases, $X^1$ is Sr. In certain other cases, $X^1$ is Zn. In some instances, $X^1$ is Mn.

In certain embodiments of a dimeric HCA compound of formula (VII), the second HCA compound is selected from one of the following groups:

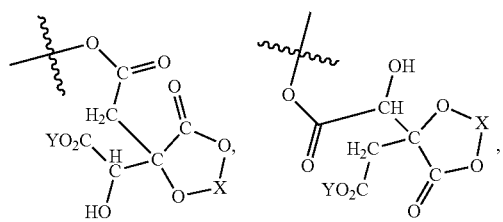

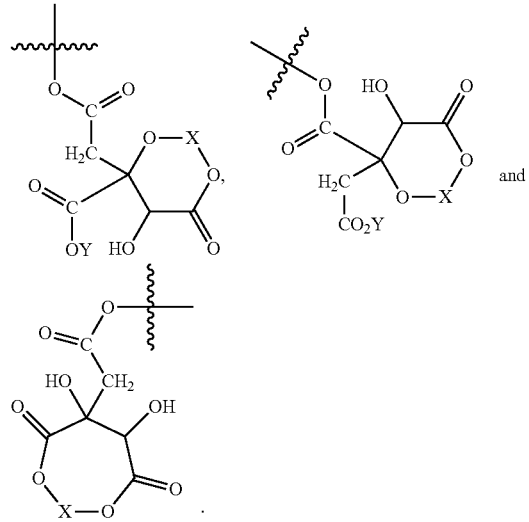

In certain embodiments of a dimeric HCA compound of formula (VII), the second HCA compound is the following group:

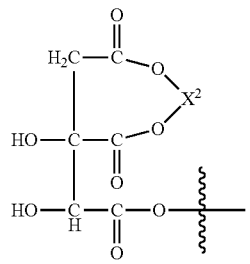

In certain embodiments, the dimeric HCA compound of formula (VII) is a dimer of formula (VIII):

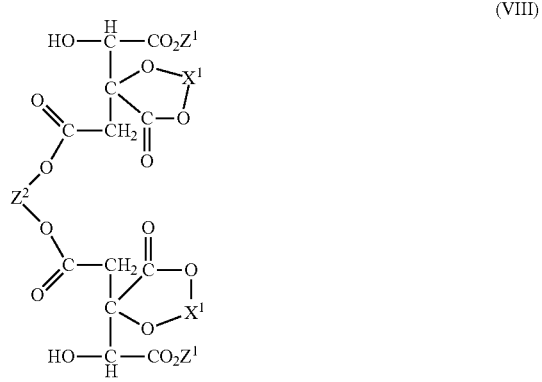
(VIII)

wherein $X^1$ and $Z^2$ are each independently a divalent metal selected from Group IIA metals, Group IIB metals and Group VIIA metals; and each $Z^1$ is independently hydrogen or a monovalent metal.

In some embodiments of a dimeric HCA compound of formula (VII) or (VIII) $X^1$, X and one of $Z^1$ or $Z^2$ is selected from Mg, Ca, Sr, Ba and Ra. In some cases, $X^1$, X and one of $Z^1$ or $Z^2$ is selected from Mg, Ca, Sr, Ba and Ra. In some cases $X^1$, X and one of $Z^1$ or $Z^2$ is Mg. In some cases $X^1$, X and one of $Z^1$ or $Z^2$ is Ca. In other cases $X^1$, X and one of $Z^1$ or $Z^2$ is Sr. In other cases $X^1$, X and one of $Z^1$ or $Z^2$ is Ba. In some other cases $X^1$, X and one of $Z^1$ or $Z^2$ is Ra.

In some embodiments of a dimeric HCA compound of formula (VII) or (VIII) $X^1$, X and one of $Z^1$ or $Z^2$ is a Group IIB group metal. In certain cases, $X^1$, X and one of $Z^1$ or $Z^2$ is Zn.

In some embodiments of a dimeric HCA compound of formula (VII) or (VIII) $X^1$, X and one of $Z^1$ or $Z^2$ is a Group VIIA group metal. In some cases, $X^1$, X and one of $Z^1$ or $Z^2$ is Mn.

In some embodiments of an HCA compound of formula (VII) or (VIII) $Y^1$-$Y^4$, Y and one of $Z^1$ or $Z^2$ are each independently a Group IA metal. In some cases, the Group IA metal is selected from Li, Na and K. In certain cases, the Group IA metal is K.

In some embodiments of a dimeric HCA compound of formula (VII) or (VIII) at least one of $Y^1$-$Y^4$, Y and one of $Z^1$ or $Z^2$ is H.

In certain embodiments of a dimeric HCA compound of formula (VII) or (VIII), each HCA compound is (−)-hydroxycitric acid.

In some cases a dimeric compound of formula (VII) or (VIII) is present in a substantially pure form. The subject methods of preparation provide for preparation of dimeric compounds, e.g., a compound including two and only two molecules of HCA per 3 divalent metals (X) and two monovalent metals (Y), without formation of a mixture of dimeric and/or monomeric HCA and its corresponding lactone forms. In certain other cases the dimeric hydroxycitric acid (HCA) metal compounds of formula (VII) or (VIII) are provided in combination with the subject monomeric HCA compounds. In some cases, a compound of formula (VII) or (VIII) is provided by dimerization of HCA bimetal compounds of formula (I), such as formulas (1A) or (1B).

In certain instances, the subject dimeric HCA compound of formulae (VI)-(VIII) is a compound of Table 4. In certain instances of a compound of Table 4, both HCAs are (−)-hydroxycitric acid.

TABLE 4

Compounds of interest of Formula (VI)-(VIII)

| Compound of Formula (VI)-(VIII) | X and $Z^1$ or $Z^2$ | $Z^1$ or $Z^2$ |
|---|---|---|
| 1 (2Li3Mg2HCA) | Mg | Li |
| 2 (2Li3Ca2HCA) | Ca | Li |
| 3 (2Li3Sr2HCA) | Sr | Li |
| 4 (2Li3Zn2HCA) | Zn | Li |
| 5 (2Li3Mn2HCA) | Mn | Li |
| 6 (2Na3Mg2HCA) | Mg | Na |
| 7 (2Na3Ca2HCA) | Ca | Na |
| 8 (2Na3Sr2HCA) | Sr | Na |
| 9 (2Na3Zn2HCA) | Zn | Na |
| 10 (2Na3Mn2HCA) | Mn | Na |
| 11 (2K3Mg2HCA) | Mg | K |
| 12 (2K3Ca2HCA) | Ca | K |
| 13 (2K3Sr2HCA) | Sr | K |
| 14 (2K3Zn2HCA) | Zn | K |
| 15 (2K3Mn2HCA) | Mn | K |

HCA Compositions and Additional HCA Compounds

This disclosure provides HCA compositions including one or more of any of the monomeric and dimeric compounds described herein. In some cases, the subject composition includes a HCA metal compound of one of formula (I), (IA), (IB) and (II) plus at least a second HCA-containing component. The subject HCA compositions can be composed primarily of one or more monomeric compound(s).

By "composed primarily of" is meant the composition includes 50% by weight or more of monomeric HCA compound, such as 60% or more, 70% or more, 80% or more, 90% or more, 95% or more, or even more relative to other HCA containing components of the composition. The subject HCA compositions can include a mixture of monomeric and dimeric HCA-containing compounds. In some cases, a composition including primarily dimeric HCA compounds is utilized. Any convenient HCA containing species can find use in the subject compositions. HCA compounds of interest include those described by Clouatre et al. in PCT Application Serial No. US2017/050759 filed Sep. 8, 2017, the disclosure of which is herein incorporated by reference in its entirety.

In one embodiment there is provided an HCA composition comprising, a first monomeric HCA compound according to formulae (I), (IA), (IB) or (II) (e.g. as described herein) and a second monomeric HCA compound of formula (III):

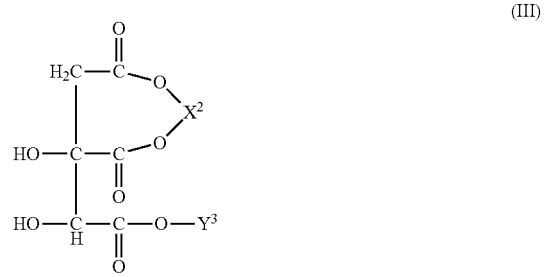

(III)

wherein, $X^2$ is a divalent metal selected from Group IIA metals, Group IIB metals and Group VIIA metals, and $Y^3$ is a monovalent metal, or a hydrate thereof.

In Formula (III), $X^2$ can be a Group IIA group metal. In Formula (III), $X^2$ can be selected from Mg, Ca, Sr, Ba and Ra. In Formula (III), $X^2$ can be a Group IIB group metal. In Formula (III), $X^2$ can be Zn. In Formula (III), $X^2$ can be a Group VIIA group metal. In Formula (III), $X^2$ can be $X^2$ is Mn. In Formula (III), Y can be a Group IA metal. Sometimes, Y is selected from Li, Na and K. Optionally, Y is K.

In some embodiments of Formula (III), $X^2$ is selected from Mg, Ca, Sr, Zn and Mn; and Y is selected from Li, Na and K. Sometimes, Y is Li. Optionally, Y is Na. Alternatively, Y is K. In some cases, $X^2$ is Mg. $X^2$ can also be Ca. Optionally, $X^2$ can be Sr. In certain cases, $X^2$ is Zn. $X^2$ can also be Mn. In such cases, the HCA can be (−)-hydroxycitric acid.

In another embodiment, an HCA composition is provided comprising, a monomeric HCA compound according to formulae (I) (IA), (IB) or (II) (e.g. as described herein) and at least one additional HCA compounds of one of Formulae (III)-(VI) or a dimer thereof.

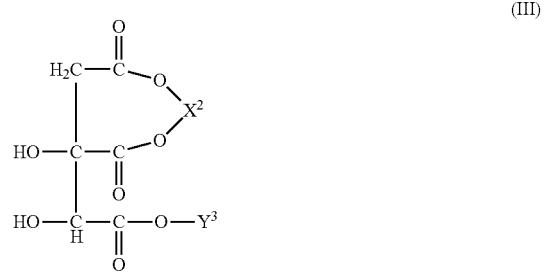

(III)

-continued

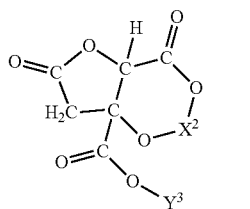
(IV)

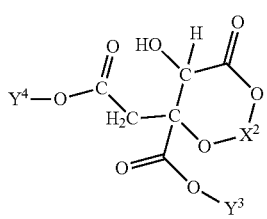
(V)

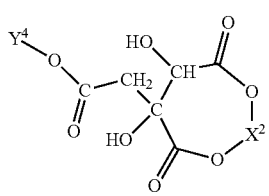
(VI)

wherein $X^2$ is a divalent metal selected from Group IIA metals, Group IIB metals and Group VIIA metals, and $Y^3$ and $Y^4$ are each independently hydrogen or a monovalent metal.

In some embodiments there is provided a pharmaceutical or nutraceutical composition comprising a substantially pure monomeric HCA compound (e.g of formulae (I)-(II) as described herein) or dimeric HCA compound (e.g., of formulae (VII)-(VIII) as described herein) and a pharmaceutically acceptable excipient. In certain embodiments, the pharmaceutical or nutraceutical composition further comprises a second compound selected from a monomeric HCA compound and a dimeric HCA compound. In certain cases, the second compound is an HCA compound as disclosed herein of formulae (I)-(II) or a dimeric HCA compound as disclosed herein of formula (VII)-(VIII).

In some embodiments, the monomeric HCA compound is a lactone of formula (IV):

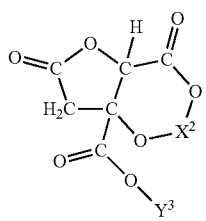
(IV)

wherein $X^2$ is a divalent metal selected from Group IIA metals, Group IIB metals and Group VIIA metals, and $Y^3$ is a monovalent metal, e.g. Na, Li, K.

In some embodiments, the monomeric HCA compound is of formula (V):

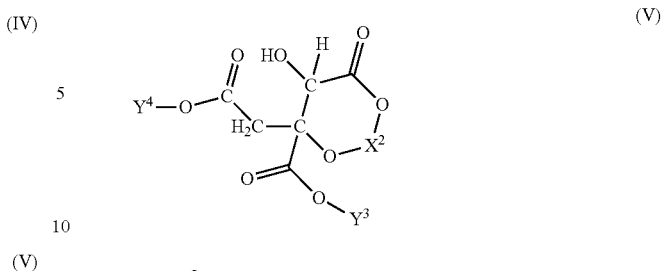
(V)

wherein $X^2$ is a divalent metal selected from Group IIA metals, Group IIB metals and Group VIIA metals, and $Y^3$ and $Y^4$ are each independently selected from hydrogen or a monovalent metal, e.g. Na, Li, K.

In some cases, when a compound of formula (IV) is contacted with an aqueous solution, the lactone compound is converted into a combination of monomeric HCA bimetal compounds, including, but not limited to compounds of formulas (V), or a hydrate thereof. In some cases when a compound of formula (IV) is contacted with an aqueous solution, the lactone compound is slowly converted to monomeric HCA bimetal compounds, to result in an equilibrium mixture of a lactone compound of formula (IV) and monomeric HCA compounds (e.g. of formulas (V)). In certain cases, the equilibrium contains about a 1:1 mixture of monomeric HCA compounds to lactone compounds. In other cases, the equilibrium contains a greater concentration of monomeric HCA compounds than lactone compounds, such that a 1.1:1, 1.2:1, 1.3:1, 1.4:1, 1.5:1, 1.6:1, 1.7:1, 1.8:1, 1.9:1 or a 2:1 mixture of monomeric HCA compounds to lactone compounds is present in the equilibrium mixture. In certain cases, the equilibrium contains about a 1.5:1 mixture of monomeric HCA compounds to lactone compounds. In other cases the equilibrium contains a lesser concentration of monomeric HCA compounds than lactone compounds, such that a 1:1.1, 1:1.2, 1:1.3, 1:1.4, 1:1.5, 1:1.6, 1:1.7, 1:1.8, 1:1.9 or 1:2 mixture of monomeric HCA compounds to lactone compounds is present in the equilibrium mixture. In certain cases, the equilibrium contains about a 1:1.5 mixture of monomeric HCA compounds to lactone compounds.

In some embodiments, the monomeric HCA compound is of formula (VI):

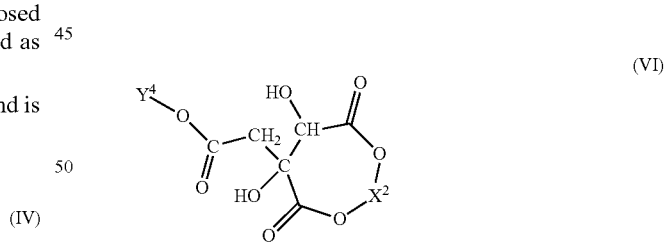
(VI)

wherein $X^2$ is a divalent metal selected from Group IIA metals, Group IIB metals and Group VIIA metals, and $Y^4$ is selected from hydrogen or a monovalent metal, e.g. Na, Li, K.

Aspects of the present disclosure include monomeric HCA compounds, lactone forms of monomeric HCA compounds and dimeric HCA compounds (e.g., as described herein), solvates, hydrates and/or prodrug forms thereof. In addition, it is understood that, in any compound described herein having one or more chiral centers (e.g., the C1 or C2 carbon centers), if an absolute stereochemistry is not expressly indicated, then each center may independently be of R-configuration or S-configuration or a mixture thereof.

It will be appreciated that all permutations solvates, hydrates, prodrugs and stereoisomers are meant to be encompassed by the present disclosure.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

In some embodiments, the subject compounds are provided in the form of a solvate (e.g., a hydrate). The term "solvate" as used herein refers to a complex or aggregate formed by one or more molecules of a solute and one or more molecules of a solvent. Such solvates can be crystalline solids having a substantially fixed molar ratio of solute and solvent. Representative solvents include by way of example, water, methanol, ethanol, isopropanol, acetic acid, and the like. When the solvent is water, the solvate formed is a hydrate.

Pharmaceutical and Nutraceutical Compositions

Also provided are pharmaceutical compositions that include a subject monomeric HCA compound, lactone thereof or a subject dimeric HCA compound. Pharmaceutical preparations are compositions that include a monomeric HCA compound, a lactone thereof, or a dimeric HCA compound or any combination thereof (for example one or more of the subject compounds, either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

Also provided are compound active pharmaceutical or nutraceutical ingredient compositions including a subject monomeric HCA compound, lactone forms thereof or a subject dimeric HCA compound (e.g., as described herein). As used herein, an active pharmaceutical or nutraceutical ingredient refers to a composition that is produced using the subject methods of preparation, where the composition may optionally be subjected to one or more further purification steps post synthesis. In general, an active pharmaceutical or nutraceutical ingredient is a composition suitable for formulation into a pharmaceutical composition. In some cases, the compound active pharmaceutical or nutraceutical ingredient composition is not purified post synthesis, such that the components of the composition reflect those products produced during the subject methods of preparation. In some embodiments, the subject active pharmaceutical or nutraceutical ingredient consists of a substantially pure monomeric HCA compound (e.g of formulae (I)-(II) as described herein) or a substantially pure dimeric HCA compound (e.g., of formulae (VII)-(VIII) as described herein). In some embodiments, the substantially pure monomeric HCA or dimeric HCA compound is the principle component of the subject active pharmaceutical or nutraceutical ingredient. As used herein, by "substantially pure" is meant a composition having a purity of 80% or more, such as 85% or more, 90% or more, 95% or more, 98% or more or 99% or more with respect to a target component, e.g., a subject HCA compound.

In certain embodiments of a pharmaceutical or nutraceutical composition as described herein, the HCA or dimeric HCA compound is selected from one or more compounds disclosed in any of Tables 1-3.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments administration to a mammal will result in systemic release of a compound of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compounds and compositions of the present disclosure are administered subcutaneously. In certain embodiments, the compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered alone or in appropriate association, as well as in combination, with other pharmaceutically active compounds.

Dose levels can vary as a function of the specific compound, the nature of the delivery vehicle, and the like. Desired dosages for a given compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

Also provided are pharmaceutical preparations of the subject compounds and the second active agent. In some instances the second active agent is a second monomeric HCA compound, or dimeric HCA compound (e.g., as described herein). In pharmaceutical dosage forms, the compounds may be administered in a pharmaceutically acceptable form, or they may also be used alone or in appropriate association, as well as in combination, with other pharmaceutically active compounds.

Dosage levels of the order of from about 0.01 mg to about 140 mg/kg of body weight per day are useful in representative embodiments, or alternatively about 0.5 mg to about 7 g per patient per day. Those of skill will readily appreciate that dose levels can vary as a function of the specific compound, the severity of the symptoms and the susceptibility of the subject to side effects. Dosages for a given compound are readily determinable by those of skill in the art by a variety of means.

The amount of active ingredient(s) that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, such as 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Also provided are nutraceutical compositions including one or more of the subject compounds. The nutraceutical composition can be administered as an oral liquid or solid dosage form. Oral solid dosage forms are well known in the art and include tablets, caplets, gelcaps, capsules, and edible food items. Oral solid dosage forms can be made with one or more pharmaceutically acceptable excipients. Pharmaceutically acceptable excipients assist or make possible the formation of a dosage form for a bioactive material and include diluents, binding agents, lubricants, glidants, disintergrants, coloring agents, and flavorants and nutrients. An excipient is pharmaceutically acceptable if, in addition to performing its desired function, it is non-toxic, well tolerated upon ingestion, and does not interfere with absorption of bioactive materials. In one aspect, the present disclosure is directed to an oral liquid dosage form including the nutraceutical composition and one or more vehicles and optional ingredients (e.g., as described herein). In another aspect, the present disclosure is directed to an oral solid dosage form that can be a tablet, a caplet, a gelcap, or a capsule that includes the nutraceutical composition and, optionally, one or more pharmaceutically acceptable excipients as is known in the art. Exemplary nutraceutical compositions and components of interest include those described in WO/2010/128949.

Also provided are cosmetic compositions including one or more of the subject compounds. Additional cosmetically or pharmaceutically beneficial ingredients can also be included in the formulated compositions of the present disclosure, which can be selected from, but not limited to skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In some instances, the cosmetically acceptable composition further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about C10 to C22, long chain fatty amines from about C10 to C22, fatty alcohols, ethoxylated fatty alcohols and di-tail phospholipids. Emollients are defined as agents that help maintain the soft, smooth, and pliable appearance of skin. Emollients function by their ability to remain on the skin surface or in the stratum corneum. The cosmetically acceptable composition of this present disclosure may include fatty ester emollients, which are listed in the International Cosmetic Ingredient Dictionary, Eighth Edition, 2000, p. 1768 to 1773.

Methods of Use

Aspects of the present disclosure include methods for modulating a variety of diseases states of interest by administration of a subject monomeric HCA compound, lactone thereof or dimeric HCA compound (e.g., as described herein) or a composition thereof. In some cases, the subject compounds are monomeric and present in a form that provides for uptake and bioavailability of the compounds in vivo. In some cases, the uptake of the compounds is enhanced when compared to other known HCA compounds. In some cases, the subject compounds are dimeric and also present in a form that provides for uptake and bioavailability of the compounds in vivo. In some cases, the uptake is comparable to other known HCA compounds. In some cases, the uptake is less than that of the subject monomeric compounds. However, the subject dimeric compounds are in a desirable biologically active form suitable for use in the subject therapeutic methods.

In some aspects, methods for alleviating at least one symptom associated with a disease state, disorder or condition of interest are provided. In some embodiments, the subject methods are methods of preventing or treating the disease state, disorder or condition of interest. Diseases and conditions of interest include those where modulation of the physiological and biochemical effects of (−)-HCA are of interest, e.g., as described by Jena et al. (Chemistry and Biochemistry of (−)-Hydroxycitric Acid from *Garcinia*." Journal of Agricultural and Food Chemistry 50(1):10-22) and Clouatre et al. (US20050032901). In some cases, conditions where the inhibition of ATP citrate lyase, inhibition of metalloproteases (e.g., Zn proteases), selective inhibition of matrix metalloproteases (see e.g., Gupta et al US Patent 20060074108), conditions related to lipid abnormalities, or metabolic diseases or conditions, are of interest.

Target diseases and conditions of interest that may be modulated or treated according to the subject methods include any convenient disease or condition where administration of HCA finds use, including but not limited to, an obesity-related condition, diabetes, an inflammatory condition, osteoarthritis, hypertension, osteoporosis, wound healing, immunomodulation, metabolic dysfunction, metabolic diseases (e.g., metabolic/insulin-resistance syndrome, type 2 diabetes) and cardiovascular disease.

Accordingly, in one embodiment there is provided a method of alleviating at least one symptom associated with a target disease or condition in a subject, the method comprising: administering to a subject in need thereof an amount of a compound of any one of formula (I), (II), (VII) or (VIII), or a composition as described herein, effective to alleviate at least one symptom associated with a target disease or condition, wherein the target disease or condition is selected from an obesity-related condition, diabetes, an inflammatory condition, osteoarthritis, hypertension, osteoporosis, wound healing, immunomodulation, metabolic dysfunction and cardiovascular disease.

In some instances of the subject methods, the target disease or condition is an obesity-related condition. Administration of the subject compounds and compositions can enhance weight loss of the subject. In some cases, the subject compounds are weight control agents that can suppress appetite and/or food intake of the subject. In certain instances, the subject is obese. In some cases, the subject can achieve a weight loss of 5% or more, such as 10% or more, 15% or more, 20% or more, 25% or more, or even more, following administration of a subject monomeric bimetal HCA compound, or composition thereof.

In some instances of the subject methods, the target disease or condition is an inflammatory condition. Inflammation is linked to the metabolic syndrome at the cellular level by way of damage to the antioxidant-defense enzyme system and mitochondria. This damage, in turn, can propagate further production of pro-inflammatory mediators Inflammatory conditions of interest include, but are not limited to, chronic inflammatory diseases (e.g., cardiovascular disease), cancer, multiple sclerosis (MS), experimental autoimmune encephalomyelitis (EAE), and oxidation stress related conditions. HCA can be useful as a protecting factor against diseases associated with oxidative stress, see e.g., Goudarzvand et al., "Hydroxycitric acid ameliorates inflammation and oxidative stress in mouse models of multiple sclerosis" Neural Regen Res. 2016 October; 11(10): 1610-1616).

In some instances of the subject methods, the target disease or condition is osteoarthritis. In some instances of the subject methods, the target disease or condition is osteoporosis. HCA can act to increase mineral retention and reduce bone loss induced by glucocorticoid-related mechanisms, see e.g., Clouatre et al. U.S. Pat. No. 6,441,041. Symptoms of interest that can be ameliorated according to the subject methods include, but are not limited to, pain, joint inflammation, loss of joint fluid, immobility of joints, legs or fingers, decreased bone density and calcification. Calcification is a term that refers to the accumulation of calcium salt in a body tissue at one location. In some cases calcifications may formed by strong chelating on protein site for example with Ca. Calcification may cause reduced cell and nerve activity. Calcification can be reduced using the subject HCA compounds. Calcified myosin has been decalcified in present of EDTA as a chelator. In a similar way, calcification can be treated using HCA and HCA compounds.

In some aspects, the present disclosure is directed to methods for inhibiting the symptoms or conditions (disabilities, impairments) associated with the target disease or condition as described in detail above. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for a particular condition or disease, but rather, can encompass a result which includes reducing or preventing the symptoms that result from the condition or disease, reducing or preventing the occurrence of such symptoms (either quantitatively or qualitatively), reducing the severity of such symptoms or physiological effects thereof, and/or enhancing the recovery of the individual after experiencing symptoms.

In some embodiments of the subject methods, the monomeric HCA compound (e.g. of formula (I), (IA), (IB) or (II)) is selected from a compound of Tables 1-3. In some embodiments of the subject methods, the monomeric HCA compound (e.g. of formula (I), (IA), (IB) or (II)) is selected from LiMgHCA, NaMgHCA, KMgHCA, LiCaHCA, NaCaHCA, KCaHCA, LiSrHCA, NaSrHCA, KSrHCA, LiZnHCA, NaZnHCA, KZnHCA, LiMnHCA, NaMnHCA and KMnHCA. In certain cases, the monomeric HCA compound is KMgHCA and has a structure of formula (I) or (II).

In some embodiments of the subject method, the dimeric HCA compound (e.g. of formula (VII) or (VIII)) is selected from $Li_2Mg_3(HCA)_2$, $Na_2Mg_3(HCA)_2$, $K_2Mg_3(HCA)_2$, $Li_2Ca_3(HCA)_2$, $Na_2Ca_3(HCA)_2$, $K_2Ca_3(HCA)_2$, $Li_2Sr_3(HCA)_2$, $Na_2Sr_3(HCA)_2$, $K_2Sr_3(HCA)_2$, $Li_2Zn_3(HCA)_2$, $Na_2Zn_3(HCA)_2$, $K_2Zn_3(HCA)_2$, $Li_2Mn_3(HCA)_2$, $Na_2Mn_3(HCA)_2$ and $K_2Mn_3(HCA)_2$. In certain cases, the dimeric HCA compound is $K_2Mg_3(HCA)_2$ and has a structure of formula (VII) or (VIII).

As used herein, the phrase "alleviating at least one symptom associated with" a disorder, disease, or condition (e.g., as described herein) denotes reversing, inhibiting the progress of, or preventing the disorder or condition to which such term applies, or reversing, inhibiting the progress of, or preventing one or more symptoms of the disorder or condition to which such term applies. Specifically, a composition of the present disclosure (such as any of the monomeric bimetal HCAL, monomeric bimetal HCA and dimeric HCA compounds disclosed herein), when administered to an individual, can treat or prevent one or more of the symptoms or conditions associated with the target disease or condition and/or reduce or alleviate symptoms of or conditions associated with these disorders. As such, protecting an individual from the effects or symptoms resulting from the target disease or condition includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present disclosure as compared to those that have not.

The methods provided herein can also be practiced in a "neoadjuvant setting," i.e., the method can be carried out before the primary/definitive therapy. In some embodiments, the individual has previously been treated. In some embodiments, the individual has not previously been treated. In some embodiments, the treatment is a first line therapy.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of compound administered can be determined using any convenient methods to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

In some embodiments, an effective amount of a subject compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a subject compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the compound is administered twice daily (qid), daily (qd), three times per day, every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors. In some cases, the dose of the subject compound is administered after meals. In certain instances, the dose of the subject compound is administered three times per day after meals.

Any of a variety of methods can be used to determine whether a treatment method is effective. For example, a biological sample obtained from an individual who has been treated with a subject method can be assayed for the presence and/or level of cells including a biomarker of the target disease or condition. Assessment of the effectiveness of the methods of treatment on the subject can include assessment of the subject before, during and/or after treatment, using any convenient methods. Aspects of the subject methods further include a step of assessing the therapeutic response of the subject to the treatment. In some embodiments, the method includes assessing the condition of the subject, including diagnosing or assessing one or more symptoms of the subject which are associated with the disease or condition of interest being treated (e.g., as described herein).

Methods of Preparation

Aspects of the present disclosure include methods for preparing a monomeric hydroxycitric acid (HCA) compound, or lactone thereof (e.g., as described herein). The subject method of preparation provides for monomeric forms of HCA that include two metals. A first step of the subject methods includes the isolation of a first divalent metal in a 5-membered heterocyclic ring of a monomeric compound, where the C2 carboxylate group and hydroxy group are bonded to the divalent metal, and the C1 and C3 carboxylates are converted to their corresponding free acids. The bonding of the HCA carboxylate and hydroxy groups to the divalent metal can be characterized as having substantial covalent character. In some cases, the first step includes acidifying a dimeric or oligomeric HCA compound including the target divalent metal, e.g., $X_3(HCA)_2$, under acidic conditions sufficient to produce a monomeric $H_2X(HCA)$ having a particular configuration. In certain cases, acidification is achieved using an aqueous solution of a strong acid, e.g., sulfuric acid. In certain instances of the method, the $H_2X(HCA)$ intermediate monomeric compound is isolated and dried prior to neutralization according to a second step of the method.

In a further step of the method, a second monovalent metal is bonded with the free carboxylic acid group at C1 or C3 of the monomeric metal intermediate, or both of C1 and C3. In some cases, the second and optionally third monovalent metal is installed via addition of an amount of YOH basic reagent sufficient to neutralize the free acid at the C1 and C3 position. In some cases, the relatively lower (i.e., more acidic) pKa of the C1 versus the C3 carboxylic acid group can direct lactone formation and subsequent installation of the monovalent metal preferentially at that C1 position when the acidification and neutralization steps of the subject methods are performed in sequence starting from a suitable dimeric or oligomeric precursor. As such, the subject methods provide for a particular configuration of metal-HCA bonds to produce the subject monomeric HCA compounds (e.g., compounds of formulae (I)-(II)).

The subject methods of preparation can proceed without formation of an undesirable mixture of dimeric and/or oligomeric HCA forms. The subject methods can also provide for preparation of monomeric bimetal compounds without formation of significant amounts of additional HCA compounds. Exemplary methods and materials for practicing the subject methods of preparation are described in the experimental section below.

In some embodiments, the method comprises:

a) acidifying dimeric $X_3(HCA)_2$ with an acidic solution under conditions sufficient to produce a monomeric $H_2X$(HCA) compound of the formula:

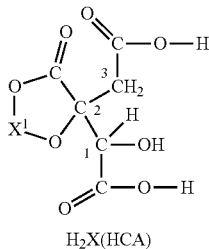

H₂X(HCA)

wherein $X^1$ is a divalent metal;

b) neutralizing the monomeric $H_2X$(HCA) compound with a YOH solution under conditions sufficient to produce a monomeric hydroxycitric acid (HCA) compound of formula (I):

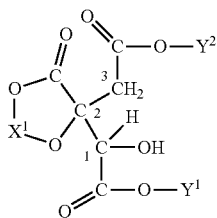

(I)

wherein $Y^1$ is hydrogen or a monovalent metal and $Y^2$ is hydrogen or a monovalent metal, wherein at least one of $Y^1$ or $Y^2$ is a monovalent metal; and c) isolating the monomeric hydroxycitric acid (HCA) compound.

In other embodiments, the method comprises:

a) acidifying dimeric $X_3(HCA)_2$ with an acidic solution under conditions sufficient to produce a monomeric HX(HCA) lactone compound of the formula:

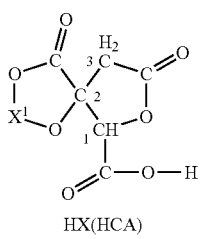

HX(HCA)

wherein $X^1$ is a divalent metal;

b) neutralizing the monomeric HX(HCA) compound with a YOH solution under conditions sufficient to produce a monomeric hydroxycitric acid (HCA) compound of formula (II):

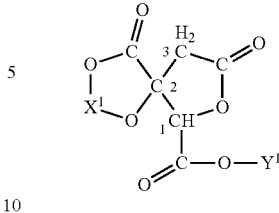

(II)

wherein $Y^1$ a monovalent metal; and c) isolating the monomeric hydroxycitric acid (HCA) compound.

In some cases, $X^1$ or $X^2$ is selected from Group IIA metals, Group IIB metals and Group VIIA metals.

Any of the subject methods can further comprise, prior to step b), isolating and drying the monomeric HX(HCA) or H₂XHCA compound. In some instances, the methods further comprise, prior to step a), contacting a sample comprising a monovalent metal HCA compound (e.g., $K_3$HCA) with a salt of the metal X to produce a dimeric $X_3(HCA)_2$ or an oligomeric form thereof. The subject precursor compounds and methods can be selected to maximize the presence or formation of lactone forms of the HCA compounds. The acidification, drying and/or neutralization steps of the subject methods can provide for formation of a monomeric bimetal HCA compound without formation of other bimetal HCA compounds or dimeric or oligomeric forms of HCA to contaminant the product composition. In other cases, the subject precursor compounds and methods can be selected to minimize the presence or formation of lactone forms of the HCA compounds. The acidification, drying and/or neutralization steps of the subject methods can provide for formation of a monomeric bimetal HCA compound (e.g. of formula (I)) without formation of lactone or dimeric or oligomeric forms of HCA to contaminant the product composition. In some cases, the subject compound composition that is isolated at the end of the subject methods is substantially pure (e.g., 80% purity or more, etc.).

In certain cases, the subject compound composition that is isolated at the end of the subject methods contains one or more HCA compounds as described herein. In certain embodiments, the isolated composition contains a HCA compound in combination with its corresponding lactone compound in an equilibrium mixture. In certain cases, the isolated composition includes one or more dimeric HCA compounds as described here.

In certain embodiments of the subject methods, a compound of formula (I) is produced where $X^1$ is selected from Mg, Ca, Sr, Zn and Mn; and $Y^1$ or $Y^2$ is selected from Li, Na and K. In some cases both of $Y^1$ and $Y^2$ are selected from Li, Na and K. In certain cases, $Y^1$ and $Y^2$ is Li. In some cases, $Y^1$ and $Y^2$ is Na. In some cases, $Y^1$ and $Y^2$ is K. In some cases, $X^1$ is Mg. In some cases, $X^1$ is Ca. In some cases, $X^1$ is Sr. In some cases, $X^1$ is Zn. In some cases, $X^1$ is Mn. In some cases, the HCA is (−)-hydroxycitric acid.

In certain embodiments of the subject methods, a compound of formula (II) is produced where $X^1$ is selected from Mg, Ca, Sr, Zn and Mn; and $Y^1$ is selected from Li, Na and K. In certain cases, $Y^1$ is Li. In some cases, $Y^1$ is Na. In some cases, $Y^1$ is K. In some cases, $X^1$ is Mg. In some cases, $X^1$ is Ca. In some cases, $X^1$ is Sr. In some cases, $X^1$ is Zn. In some cases, $X^1$ is Mn. In some cases, the HCA is (−)-hydroxycitric acid.

The following examples are offered by way of illustration and not by way of limitation.

EXPERIMENTAL

Example 1: Preparation of HCA Compounds

HCA monomeric and dimeric compounds of interest can be prepared and characterized by adapting those methods described by Clouatre et al. in PCT Application Serial No. US2017/050759 filed Sep. 8, 2017, the disclosure of which is herein incorporated by reference in its entirety.

Characterization of Compounds
Monomeric Compounds

Elemental analysis via Energy Dispersive Analysis (EDS) of KMgHCA prepared according to the methods described herein showed a mole ratio of K to Mg that was near equal, suggesting a structure of a lactone compound including potassium and magnesium five member ring as below:

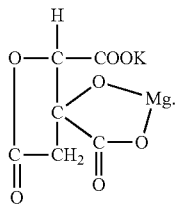

Dimeric Compounds

Based on spectrum Energy Dispersive Analysis (EDS) the atomic ratios of K to Ca or K to Mn in compound KMnHCA dimer or KCaHCA dimer were determined to be less than 1, suggesting a structure for KMnHCA dimer as well as KCaHCA dimer as follows:

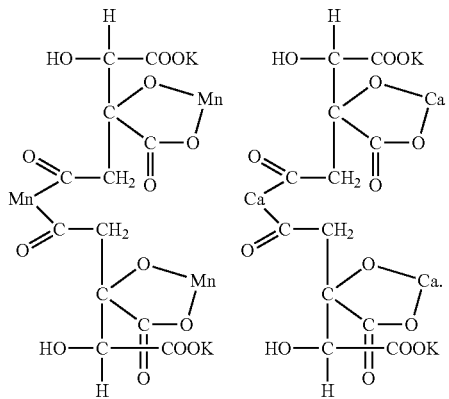

Preparation of Monomeric KMgHCA or $K_2$MgHCA from $K_3$HCA

Syrup containing $K_3$HCA (approximately 40.40% by wt) or HCA (25.72% by wt) was used in the method. The syrup further includes impurities such as gum, fiber, pectin, and garcinol etc. To prepare a HCA compound of interest from the syrup, several steps are performed:
1. Conversion of $K_3$HCA to $Mg_3HCA_2$;
2. Acidification of $Mg_3HCA$ solution; and
3. Neutralization.

This method was also performed using HCA compositions from Laila as starting material.

Materials:
a. Syrup $K_3$HCA was made according to conventional methods. HCA content of the syrup was determined by HPLC and found to be 25.72%.
b. $K_3$HCA/$Mg_3$HCA donated by Laila company, India.
c. $MgCl_2 \cdot 7H_2O$, $CaCl_2 \cdot 2H_2O$, HCl 37%, $H_2SO_4$ conc. from EMerck.

Procedure:
1. Conversion $K_3$HCA to $Mg_3(HCA)_2$ $K_3$HCA syrup was placed into a 3 liter beaker glass and diluted with distilled water. The solution has pH 11. To the solution was then added a solution of $MgCl_2 \cdot 7H_2O$ (0.791 mol., 182.8 g) in distilled water (350 mL). The mixture was warmed for 1 hour and then evaporated to a third of the volume (500 ml). After cooling overnight, crude crystals of $Mg_3$HCA (120.7 g) formed and were isolated by filtration. HCA content of the crystals was 76.36% by HPLC. Characterization with FT IR(KBr) shows $\upsilon$ ($cm^{-1}$) 3237 br., 1579, 1391 $cm^{-1}$. Ion chloride is free.

2. Acidification of $Mg_3(HCA)_2$

Dried powder of $Mg_3(HCA)_2$ was dissolved in hot distilled water. A solution of 5% sulfuric acid was added drop wise with vigorous stirring for 2 hours. After concentration of the solution volume ethanol (2× the volume of the concentrated solution) was added. The solution was reduced to a volume sufficient to allow precipitation, then the mixture was cooled to 5° C. for 5 hours to give a monomeric magnesium chelate HCA compound (e.g. of formulae $H_2$MgHCA or HMgHCA as described herein) as a white solid which was isolated by filtration.

3. Preparation KMgHCA or $K_2$MgHCA

A solution of $H_2$MgHCA or HMgHCA was dissolved in distilled water to give a resulting pH 3 solution. To this solution was added a solution of 20% KOH in distilled water until a pH of 11 was achieved. The solution was warmed for 1 hour, and then further heated to evaporate the solution and produce a solid. The solid formed (e.g KMgHCA or $K_2$MgHCA of formulae (I)-(II) as described herein) was washed with ethanol and dried in a desiccator.

4. Determination $SO_4^{-2}$ content

A 1.0 g sample of KMgHCA/$K_2$MgHCA (e.g., of formulae (I)-(II)) was placed in a crucible, and heated at 850° C. to achieve a constant weight. The residue was dissolved in distilled water (25 mL) and a solution of $BaCl_2$ titrated with oxalic acid was added.

5. Determination $Cl^-$ content

A 1.0 g sample of KMgHCA/$K_2$MgHCA (e.g., of formulae (I)-(II)) was placed in a crucible, and heated at 850° C. to a constant weight. The residue was dissolved in distilled water (25 mL) and titrated with a solution of silver nitrate.

Example 2: Preparation of Monomeric KMgHCA/$K_2$MgHCA

General Procedure:
a. In a 500 ml glass beaker, pure acid form of HCA is diluted with distilled water. Calculate number of carboxylic group. Check mol. ratio of HCA free acid to HCA lactone.
b. Add a solution of KOH using a half equivalent relative to HCA acid, and react for a period of 0.5, 1.0 or 1.5 h. Each reaction is analyzed using HPLC to obtain a molar ratio of HCA acid in the reaction mixture.
c. The conditions may be optimized to give the least amount of lactone (e.g. of formula (II)), prior to adding $Mg(HCO_3)_2$ to the product mixture. The resulting product is highly soluble in water. By crystallization fractionation, monomer KMgHCA/$K_2$MgHCA of formula (I) is recovered.

d. The product is purified and characterized using x-ray diffraction (XRD) as compared to a pure monomeric KMgHCA sample.

Example 3: Alternative Methods for Preparing Monomeric KMgHCA/K$_2$MgHCA

1. Method of making H$_3$HCA from K$_3$HCA syrup.
   Take 100 gr of K$_3$HCA (brix 74) consisting of 81% K$_3$HCA
   Dilute with 250 ml of demineralized water ("DMW")
   Add solution of CaCl$_2$.2H$_2$O (56.0 g; 0.38 mol) into 100 ml of DMW
   The precipitate is taken out, washed, dried and Ca$_3$(HCA)$_2$ white powder is obtained
   The amount of white powder Ca$_3$(HCA)$_2$ is 70.78 g with 20.9% of Ca
   Mix the powder and 500 ml of DMW, producing a slurry
   The slurry is then loaded onto an acid cation resin exchange column
   The soluble eluate/filtrate is then loaded onto a strong anion exchange column.
   The product soluble eluate/filtrate (420 ml) is cleaned using activated carbon 1 g at 60° C. to give a clean HCA free acid.
2. Quality of the HCA free acid solution
   The eluate/filtrate obtained above is then concentrated under reduced pressure at 60° C. to give a residue.
   The residue was extracted using dry acetone followed by dry ether.
   The insoluble part yields a white solid.
   The filtrate part is evaporated to dry.
   The white solid part is analyzed using HPLC and indicates that using this method, lactones are not formed.
3. Method of making monomeric KMgHCA
   The process of making H$_3$HCA is repeated as described in section above and HCA free acid is obtained
   250 ml of a solution having 0.1 mol H$_3$HCA is obtained
   Mg(OH)$_2$ slurry (5.8 g; 0.1 mol) in 10 ml of DMW is added and the mixture left for 2 hours
   A solution of KOH (5.6 g; 0.1 mol) in 10 ml of demineralized water (DMW) is added. The pH of the mixture is observed to be 9-9.5
   20 ml of ethanol is added into this solution and 2 layers form.
   The top layer is separated, then ethanol added to achieve 70% ethanol.
   The bottom layer is separated and dried under vacuum
   A white solid is obtained, and washed using dry methanol
   White dry solid (20.0 g; 48.5%). Consisting of Mg 5.8%; K 9.42%. This analysis is close to theoretical for the formula KMgHCA.8H$_2$O
4. Method of making monomeric KMgHCA
   The process of H$_3$HCA making is repeated as described in section above and HCA free acid is obtained
   200 ml of a solution consisting of 0.1 mol H$_3$HCA is obtained
   The H$_3$HCA is partially neutralized using a solution of KOH (5.6 g; 0.1 mol) in 10 ml demineral water.
   Into the solution, a Mg(OH)$_2$ slurry (5.8 g; 0.1 mol) is added to form a white suspension.
   The mixture is heated at 60° C. for 1 hour, producing a clear solution
   The pH of the solution is adjusted to pH 9 by addition of a KOH solution. Then 20 ml of alcohol is added resulting in 2 layers.
   The top layer is separated and a further portion of ethanol added resulting in a solution of approximately 70% ethanol. This mixture forms 2 layers.
   The bottom layer is separated, then dried under vacuum, and then washed using dry methanol
   Dried insoluble material gave 35.5 g of white powder (86.2%) consisting Mg5.9% and K9.6%. This analysis is close to the formula of KMgHCA.8H$_2$O
5. Method of making monomeric KMgHCA using MgCl$_2$
   10 g of K$_3$HCA syrup (brix 74) consisting of 81% K$_3$HCA is obtained
   Dilute with 20 ml of DMW
   Bleached with activated carbon (2 g in 20 ml of DMW), filtered.
   Take 40 ml of solution consisting K$_3$HCA (8.1 g, 0.025 mol)
   Add solution of MgCl$_2$.6H$_2$O (5.075 g; 0.025 ml) into 10 ml of DMW
   Into the reaction mixture, add in 60 ml of ethanol (98% pure)
   Stir for 1 day period, then remove the upper layer
   Add 300 ml of ethanol 98% to the upper layer solution. Stir for 1 day to extract Cl
   The upper layer solution containing Cl is then removed and the bottom layer is extracted by adding 100 ml of ethanol 98%
   Filtrate is separated, and insoluble part is dried under vacuum resulting in a white powder.
   The powder is washed with dry methanol, and dried. The solid product is 7.0 g (67%) consisting K 9.5% and Mg 5.8% this is likely KMg HCA.8H$_2$O
6. Method of making monomeric KMgHCA using strong anion resin
   20 g of K$_3$HCA syrup (brix 74) consisting 81% K$_3$HCA (16.2 g; 0.05 mol K$_3$HCA)
   Dilute with 100 ml of DMW
   Bleach with 4 g of activated carbon and filter out solids
   Filtrate is made into pH 5.5 using additional HCl
   This solution is loaded onto an anion exchange column, (strong anion resin type)
   A solution consisting of KH$_2$HCA containing partially substituted K$^+$ was obtained
   Mg(OH)$_2$ slurry 0.025 mol was added and then heated at 60° C. give a solution.
   The solution consist of KMgHCA (see section 4)
7. Method of making of H$_3$HCA from K$_3$HCA syrup.
   In another method, the process begins with fresh fruit to produce a K$_3$HCA syrup and then proceeds to through the production of H$_3$HCA to the production of a monomeric KMgHCA as follows using a Mg(OH)$_2$ method:
   100 g of K$_3$HCA (brix 74) consisting of 81% K$_3$HCA
   Dilute with 250 ml of demineralized water
   Add solutions of CaCl$_2$.2H$_2$O (56.0 g; 0.38 mol) into 100 ml of DMW
   The precipitate is taken out, washed, dried and Ca$_3$(HCA)$_2$ white powder is obtained
   The amount of white powder Ca$_3$(HCA)$_2$ is 70.78 g with 20.9% of Ca
   Mix the powder and 500 ml of DMW, producing a dough
   The dough is then filled into acid cation exchange column
   Extracted soluble is then passed into strong anion exchange column.
   Producing Cl which consisted in cation exchange regeneration
   Product of soluble is 420 ml. Then it is cleaned using activated carbon 1 g in 60° C.

Filtrate which is obtained is then concentrated using vacuum

This concentrated liquid is extracted using dry ester-asetone

The insoluble part became white solid

Filtrate part is steamed until it is dried. There's almost no residue (indicating that using this procedure there is very little lactone formation occurring)

White solid part is tested by HPLC, to confirm that no lactones are formed.

8. KMgHCA monomer making

The process of $H_3HCA$ making is repeated and HCA free acid is obtained 250 ml of the solution are having 0.1 mol $H_3HCA$ Add $Mg(OH)_2$ dough (5.8 g; 0.1 mol) into 10 ml of DMW and leave it for 2 hours Then KOH solution (5.6 g; 0.1 mol) is added into 10 ml of DMW. The pH is 9-9.5

20 ml of alcohol is added into this soluble and it forms 2 layers

Top layer is separated, then it's changed into ethanol 70%

Bottom layer is separated, steamed in vacuum

White solid is obtained, and being washed using dry methanol

We obtain white dry solid (20.0 g; 48.5%). Consisting Mg 5.8%; K 9.42%. KMgHCA.$8H_2O$

Example 4: Preparation of $Ca_3(HCA)_2$, $HCaHCA/H_2CaHCA$, $KCaHCA/K_2CaHCA$ 1. Preparation of KCaHCA
The preparation is involving in 3 steps:
a. Preparation $Ca_3(HCA)_2$ A solution containing 78.4 gram, 0.24 mole $K_3HCA$ was made up to 500 ml. By addition slowly of the solution $CaCl_2$ 50% the solution mixture reaches a pH of 8 while stirring. The solid formed was filtered, washed with water to free chloride. The solid was dried, and provided 62.25 grams of $Ca_3(HCA)_2$.

b. Preparation of $HCaHCA/H_2CaHCA$ $Ca_3(HCA)_2$ was suspended in water. The pH was adjusted to 5 by adding a solution of 0.05 N sulfuric acid. The solution was separated from the solid. Then evaporated to ⅓ volume. The mixture is then refiltered. The solution obtained is solidified after the addition of ethanol. The amorphous solid was isolated by filtration, and washed with ethanol, allowed to dry in air for 5 hours and finally dried under vacuum to provide $HCaHCA$ or $H_2CaHCA$.

b. Neutralization of $HCaHCA/H_2CaHCA$ $HCaHCA/H_2CaHCA$ was dissolved in water then neutralized by the addition of a solution of KOH 20% to pH=11. Ethanol is added to the solution mixture which then formed a white solid precipitate. After filtration, the white precipitate is dried under vacuum to provide KCaHCA or $K_2CaHCA$.

Example 5: Preparation of $Zn_3(HCA)_2$, $HZnHCA/H_2ZnHCA$, $KZnHCA/K_2ZnHCA$ b. Conversion $K_3HCA$ to $Zn_3(HCA)_2$ Into a 2 liter beaker glass, $K_3HCA$ solution 100 gr containing 11.2% $K_3HCA$ or equal to 11.2 grams, 0.0348 mol $K_3HCA$ was placed in a beaker glass. The solution was increased in volume up to 250 ml by the addition with distilled water. A solution of $ZnCl_2$ 20% was added slowly, until the pH was reduced to 5. The solid precipitated, was then filtered. The obtained precipitate was washed with distilled water two times until free of chloride. The solid was dried in a vacuum desiccators yielding 11 gr. M.P 174° C. dec.

The spectroscopy FT-IR showed wave number $\upsilon$ ($cm^{-1}$) 3441 slight broad shows OH secondary group, 1570 ($COO^-$) as fully salt, other peaks 1404, 1257, 1080, 918 and 860. The product was identified as $Zn_3(HCA)_2$.

TGA analysis of $Zn_3(HCA)_2$ is performed. From the analysis TGA obtained 2 molecules $H_2O$ or 6.61%. HCA contain 61.92%. Analysis SSA found Zn=30.45%

HPLC Analysis 11 mg $Zn_3(HCA)_2$ was placed in a 10 ml volumetric flask, then dissolved in 10 ml buffer solution $(NH_4)_2HPO_4$ to have 10 mM.

HPLC analysis shown the area observed was 2169.578 it was equal to 685.7073 ppm. The percentage of HCA in $Zn_3(HCA)_2$=685.7073 ppm/1100.0 ppm×100%=61.97%.

Based on the data results Zn=30.45%, HCA=61.97% (HPLC), $H_2O$=5.62% (TGA), the formula can be describe as $Zn_3(HCA)_2.2H_2O$. MW estimated 642.17 c. Acidified of $Zn_3HCA$ to Give $HZnHCA/H_2ZnHCA$

A dried powder of $Zn_3(HCA)_2$ was dissolved in distilled water then HCl 11% was added until a pH=~3 was obtained. The resulting mixture was stirred until dissolved, then filtered. Ethanol was added to the filtrate and the solid formed was filtered, dried under vacuum to obtain HZnHCA or $H_2ZnHCA$.

d. Preparation $ZnKHCA/ZnK_2HCA$ $HZnHCA/H_2ZnHCA$ was dissolved in water until pH 4. To this solution was added a solution of KOH 20% in water to achieve a pH of 11. The solution was warmed for 1 hour, then ethanol was added and a white solid precipitate formed. After filtration, the solid was dried in a desiccator to give $ZnKHCA/ZnK_2HCA$.

Example 6: Preparation of $Mn_3(HCA)_2$, $HMnHCA/H_2MnHCA$, $KMnHCA/K_2MnHCA$ Conversion $K_3HCA$ to $Mn_3(HCA)_2$ 116 g $K_3HCA$ solution, containing 22,258 gr., 0.0654 mol $K_3HCA$ was added to a solution made from 160 ml dry ethanol and $MnCl_2.2H_2O$ (16 g, 0.0981 mol) to give, pH=5. The mixture was warmed for 30 minutes. After addition of a further 50 ml dry ethanol and settling for 5 minutes, a pink precipitate was formed, filtered, and washed with dry ethanol. $Mn_3(HCA)_2$ was dried under vacuum wet 22.8 gram. M.p 200° C. dec.

FT-IR spectrographic data for $Mn_3(HCA)_2$ presented highly water content due to wave number 3500-2770 $cm^{-1}$; other peaks included 3838, 3741, 1558, 1408, 1064, 910, 852 and 632 $cm^{-1}$. Water could be take place in the secondary valance of $Mn^{2+}$. This was taken to the further reaction before purification.

TGA analysis of $Mn_3(HCA)_2$ is performed. TGA analysis obtained 3 molecules $H_2O$ or 8.58% and HCA content of 60.06%.

Potentiometric titration found Mn=26.23%.

HPLC analysis was performed to determine the HCA concentration.

11.9 mg $Mn_3(HCA)_2$ was placed in a 10 ml volumetric flask, then dissolved in 10 ml buffer solution $(NH_4)_2HPO_4$ 10 mM. HPLC analysis shown the area observed was 2261.905 it was equal to 714.8878 ppm. The percentage of HCA in $Mn_3(HCA)_2$=714.8878 ppm/1190.0 ppm×100%=60.06%.

Results Mn=26.23%., HCA=60.06% and $H_2O$=8.58%. The formula is $Mn_3(HCA)_2.3H_2O$.

Acidification of $Mn_3HCA_2$ $Mn_3(HCA)_2$ was added to distilled water and stirred. Then a solution of HCl 11% was added until pH=5. The mixture was then filtered and dry ethanol was added to the filtrate d to form a solid precipitate. The precipitate was filtered and dried to obtain $HMnHCA/H_2MnHCA$.

Preparation of $KMnHCA/K_2MnHCA$ $HMnHCA/H_2MnHCA$ was dissolved in distilled water followed by addition of KOH ethanolic solution 20% to pH=7. Dry ethanol was then added to precipitate a solid. The solid was isolated by filtration, washed with ethanol and dried in vacuum desiccators to obtain $KMnHCA/K_2MnHCA$.

Example 8: Conductivity of Solutions

The structure of the subject compounds (e.g., as described herein) can be deduced using a conductance meter to observe the extent of dissociate of the first and/or second metals from the compounds. In an experiment described below equimolar samples and comparative electrolyte conductance to K-acetate solution as a standard, data may be obtained which is characteristic of electrolyte binary conductants. By using a highly ionic compound, such as KCl, as a standard for conductivity in equimolar solutions, results show a similarity curve. The KMgHCA solution in water may have a pH 8-10 depending on the concentration. Under this condition, the heterocyclic anion formed will tend toward a stable form rather than an ionizable one.

In contrast, in a solution of $Mg_3(HCA)_2$, a dimeric HCA form, the ionic form will be available as a solution with a pH below 7. This can be dissolved in water by a dissolution process, meaning that $Mg_3(HCA)_2$ still presents as a dimer and not as a binary solution form.

Experiments

Several experiments investigating the electrical conductivities of solutions of KMgHCA, KZnHCA and KMnHCA are performed. The equipment used is HACH Conductivity/TDS meter, P/N=4460-00.

Materials: $KMgHCA.4H_2O$, $KZnHCA.2H_2O$, $KMnHCA.2H_2O$ are prepared using methods described herein. $KC_2H_3O_2$ and $Mg_3(CH_3O_2)_2.4H_2O$ was obtained from Merck. $H_2O$ used was demineralized water.

General procedure: All the HCA compounds and Acetate were weighed and placed in a volumetric flask and dissolved with demineralized water to one liter solution and then they were tested the conductivity (EC).

The data obtained is summarized below in Table 2:

Results:

1. Contribution κ (Value of Electrical Conductivity)

At the beginning study (run 1), it was necessary to know what was likely κ (value of electrical conductivity) resulting of ionic compound made of strong electrolyte with weak electrolyte such as $CH_3COOK$. This salt in water is dissociated completely gave κ=56.06 μS/cm.

2. Mg—O Bond κ Value

Run 2 shows the result 2 bond of Mg—O contribution approx 60.25-56.06 is 4.19 μS/cm. For 2 bond dissociate gave κ value contribution 2.095 in μS/cm. This low value is resulting by the dissociated degree much lower compared to K—O bond.

Since κ value is affected also by ionic charged, +2 higher than +1, then $Mg^{2+}$ should be given higher contribution to κ value $K^+$. It means that the solution has low concentration $Mg^{2+}$ and implies a low value of dissociation degree of Mg—O. As a conclusion, bonding Mg—O is likely covalent polar, low ionic degree.

3. Effect of OH Function

To check the electrical function of hydroxy, then run 3 and 4 was done. There was not a significant change in κ value. Based on this result, the OH group in HCA has no direct effect on variations in κ value.

4. Effect of Zn and Mn in HCA

The qualitative ionization degree has a correlation to electrical conduction (κ values) in a solution. A lower κ values of a solution has a good indication lower ionic bond character in the matter. The experiment results shown run 5 and 6 gave κ values 59.8 and 57.7 in μS/cm for Mn and Zn respectively. This value is much lower compared to KMgHCA at the equal molar solution. Therefore Zn—O bond is more covalent polar than Mn—O and more covalent then Mg—O. The experiment 7 and 8 was made equimolar solution of $Mg^{2+}$. The result κ values were relatively low. The overall conclusion is bonding of Mg, Zn and Mn with O is likely covalent polar.

5. Theoretical View Ionic Bond Character

A most famous theory for ionic bond bond character was proposed by Hanny and Smyth. The equation is shown below:

$$\% \text{ ionic character in A-B bond} = [0.16(\chi_A - \chi_B) + 3.5 (\chi_A - \chi_B)^2]\%$$

$\chi_A$ and $\chi_B$ are represented for electronegativity A and B element.

Compound KMgHCA is containing two covalent bond polar, K—O and Mg—O bond.

Ionic character K—O=[0.16 (3.44−0.82)+3.5 (3.44−0.82)$^2$]% eq to =24.45%.

Ionic character Mg—O=[0.16 (3.44−1.31)+3.5 (3.44−1.31)$^2$]% eq to =16.22%.

| Run | Materials | Molecular weight | Weight (mg) | Concentration mmol/l | additive | E. C (μS/cm) |
|---|---|---|---|---|---|---|
| 1 | $KC_2H_3O_2$ | 98.15 | 29.4 | 0.3 | — | 56.06 |
| 2 | $KMgHCA·4H_2O$ | 340.46 | 102.1 | 0.3 | | 60.25 |
| 3 | $KMgHCA·4H_2O$ | 340.46 | 102.1 | 0.3 | 10 mg gliserol | 60.23 |
| 4 | $KMgHCA·4H_2O$ | 340.46 | 102.1 | 0.3 | 10 mg glucose | 60.29 |
| 5 | $KMnHCA·2H_2O$ | 335.10 | 100.5 | 0.3 | | 59.8 |
| 6 | $KZnHCA·2H_2O$ | 345.54 | 103.7 | 0.3 | | 57.7 |
| 7 | $Mg_3(HCA)_2·2H_2O$ | 446.12 | 44.6 | 0.1 | | 31.2 |
| 8 | $Mg(CH_3COO)_2·4H_2O$ | 214.46 | 64.3 | 0.3 | | 32.3 |

In a similar manner ionic character can be estimated for Mn—O and Zn—O bond found as 12.80 and 9.63% respectively.

Covalent character as conclusion K—O=75.55%., Mg—O=83.78%., Mn—O=87.20% and Zn—O=90.37%. This means that all heterocyclic rings have a covalent character.

Example 9: Weight Loss and Reduced Inflammation

Subject Complaint: Edema, pain in legs, darkening of skin
Subject and Treatment Summary:
1. Sex: Female
2. Age: 50 years
3. Weight before treatment: 60 kg
4. General health before treatment: fairly good
5. Medical complaints: lack of energy, bone of legs inflamed (painful) after walking
6. Bimetal HCA Regimen:—KMg HCA, KCa HCA mixed powder.
   Dosage: 200 mg, 3 times a day after meals
   either consumed with plain water or juice of pineapple, tomato—or simply chewed and swallowed
7. Side effects: none
8. Progressive change in patient: In second month of treatment, the patient reduce weight to 55 kg, in the third month reduced to 52 kg and pain/inflammation in legs reduced in frequency. In the sixth month reduce to 48 kg with inflammation gone.

A woman aged 50 years previously in fairly good health, developed edema in her legs and 60 kg overweight leading to inflammation in legs as well as some darkening of the skin. A mixture of 150 mg KMg HCA and 50 mg KCa HCA was administered 3 times per day in water for 120 days. During this period she lost 12 kg of weight and her legs condition return to normal. No side effects were reported.

Example 10: Treatment of Inflammation and Joint Damage in Knees

Subject and Treatment Summary:
1. Sex: Female
2. Age: 44 years
3. Weight before treatment: 90 kg
4. General health before treatment
   blood pressure 150/90
   HDL 1.4 mg/L
   LDL 2.6 mg/L
5. Specific medical complaint:
   High inflammation in her legs, mainly in her knees. During night, it was like flame in the whole legs. She required periodic injection of fluid into her knees.
6. Doctor's Diagnosis: X-ray left knee joint shows lost joint fluid. Degenerative changes are noted in the patella-femoral and knee joint. Multiple dense loose bodies are seen in the left knee joint. Narrowing of the knee joint space is noted.
7. Bimetal HCA Regimen:—150 mg KMg HCA and 50 mg Ca HCA powder
   3 times a day after meals
   Drink with juice, tomato, pineapple, strawberry.
8. No side effects
9. Progressive change to patient condition:
   Little reported reaction for 4 months. In the fifth month after initiation of treatment, a dramatic improvement in the legs was observed. Subsequently, a μX-ray was obtained, which showed an increase in lubricating fluid in the left knee joint, indicating the joint was successfully treated although not yet completely healed. Blood pressure improved to the range of 140-130 over 90-80.

Results:
Women aged 44 year, 90 kg in weight along with knee joint problem. Her feeling was awful and medical diagnosis was losing fluid in knee joint. A mixture of bimetal HCA compounds 150 mg KMg HCA and 50 mg Ca HCA was administered 3 times per day in water for 120 days. During this period she has returned to normal in her legs. She reported good sleep. No side effects were reported.

Example 11: Treatment of Severe Osteoarthritis in Knees and Hands

Subject and Treatment Summary:
1. Sex: Female
2. Age: 86 years
3. Wight before treatment: 40 kg
4. General health: not available
5. Specific Medical Complaint: pain in joints of legs and fingers caused immobility
6. Doctor diagnosis: not available
7. Bimetal HCA Regimen:—KMg HCA, KCa HCA powder 100 mg to 150 mg
   2 times a day after meal ("chewed")
8. No side effects reported
9. Chronology of progressive change: After taking the preparation for 3 days, the pain disappeared totally and fingers could be moved freely. The sustainability was 3-7 days without consuming bimetal HCA before return of original complaint. Symptomatic relief returned soon after taking bimetal HCA.
10. No medical confirmation Notes:
The subject "chewed" aprpox. 100 mg of a mixture of the bimetal HCA compositions, morning and evening. Dosage was later increased to 150 mg twice a day. The subject's overall health and arthritis in her hands and knees is reported to be improved.

Example 12: Symptomatic Relief of Osteoarthritis in Legs

Subject and Treatment Summary:
1. Sex: Female
2. Age: 61 years,
3. Weight before treatment: 72 kg
4. General health: Uric acid 7.8 mg/dl; cholesterol 201 mg/dl
5. Specific medical complaint: subject cannot walk due to osteoartrosis genu bilateral in her legs
6. Bimetal HCA Regimen:—KMg HCA, KCa HCA powder 200 mg after meals
   3 times per day
   Consumed with juice
7. No side effects reported
8. Chronology of progressive change:
   in 3 days subject could stand on her feet
   in 10 days subject could walk
   in 14 days subject could do work
9. No medical report after healing

Example 13: Comparison of Different Bimetal Regimes (KMg vs. KCa vs. Combination)

Subject I: a women, 86 years, 40 kg (cited in Example 11, above)

Problem: osteoporosis and calcification on hand and leg (suspected); discomfort and greatly reduced use of hands/mobility
Subject II: a women, 69 years; 72 kg
Problem: osteoporosis and calcification on leg (doctor diagnosis); discomfort and greatly reduced mobility
Treatment: A. Mixture 25% KCa HCA+75% KMg HCA bimetals (100-200 mg)
B. Only KMg HCA bimetal
Results: Table 1

|         | Treatment |            |
| ------- | --------- | ---------- |
| Patient | A         | B          |
| I       | ++        | Not tested |
| II      | ++.       | +−         |

++: very good performance
+−: good but slight complaint

Treatment A: Administration of 100-200 mg of the mixed composition, 3 times a day (after meals) gave excellent reduction in symptoms for both subjects. Additional KCa HCA can be administered to treat a lack of calcium in blood and also to supply Ca to the subject for maintaining equilibrium of Ca for production of bone.
Treatment B: Only KMg HCA but not KCa HCA was used. Subject II reported partial reduction of symptoms. Subject II had slight complaint on her leg. Following treatment 2, the observed result was that she could stand on her feet.

Example 14: Comparison of KCaHCA and/or KMgHCA Compositions

Subject: Female (cited as Example 12, above)
Age: 61 years
Problem: Osteoporosis
Treatment: Materials were consumed 3 times a day after meals.
Experiment 1. Blending 150 mg KMgHCA.8H$_2$O+50 mg KCaHCA.3H$_2$O
 A 200 mg mixture of KCaHCA (25%) and KMgHCA (75%) prepared according to the subject methods was used. The actual percentage of calcium was (40/338)×25%=2.96%. Since KCaHCA.3H$_2$O was used the percentage of magnesium in the composition was (24/412)×75%=4.37%. Since KMgHCA.8H$_2$O was used, the ratio Ca:Mg=0.15: 0.36 in mmol.
Experiment 2. 200 mg KMgHCA.8H$_2$O
Experiment 3. 200 mg KCaHCA.3H$_2$O
Results:
Experiment 1 gave very good results. In three days the subject could stand on her feet, in 10 days she could walk, in 14 days she could walk freely. The observation was continued for 3 months. In the fourth month, treatment by experiment 2 was started by administration of 200 mg doses of KMgHCA. The patient was slight difficult to walk because feeling of burning sensation in her feet. Subject complained that her leg felt hot. The experiment 2 regimen was continued for a month.
Subsequently (in the next month), treatment was continued according to experiment 3. The patient received 200 mg bimetal KCaHCA. Administration using experiment 3 conditions was continued for a few days, but was then stopped due to deterioration in subject's condition to the point that she became unable to move her leg. Treatment according to experiment 1 was started.
These results indicate that the patient experienced a reduction in symptoms of osteoporosis under treatment with 200 mg blended mixture of KCaHCA/KMgHCA (150 mg KMgHCA with 50 mg KCaHCA). In Experiment 2, the patient showed a partial improvement of symptoms of osteoporosis. Administration of KCaHCA alone in experiment 3 was not effective. Use of a blend of 150 mg KMgHCA with 50 mg KCaHCA is an excellent treatment for osteoporosis.

Although the particular embodiments have been described in some detail by way of illustration and example for purposes of clarity of understanding, it is readily apparent in light of the teachings of this invention that certain changes and modifications may be made thereto without departing from the spirit or scope of the appended claims.

Accordingly, the preceding merely illustrates the principles of the invention. Various arrangements may be devised which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:
1. A pharmaceutical or nutraceutical composition, comprising:
 a pharmaceutically acceptable excipient;
 a monomeric hydroxycitric acid (HCA) compound of Formula (I):

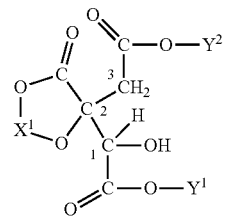

wherein:
 $X^1$ is a divalent metal selected from Group IIA metals, Group IIB metals, Mn, Tc and Re; and
 $Y^1$ is hydrogen or a monovalent metal; and
 $Y^2$ is hydrogen or a monovalent metal, or —$OY^2$ is absent and the hydroxyl of C1 is cyclically linked to the C3 carbonyl group to provide a lactone form of the compound;

or a hydrate thereof; and
an additional HCA compound of one of Formulae (III)-(VI), or a dimer thereof:

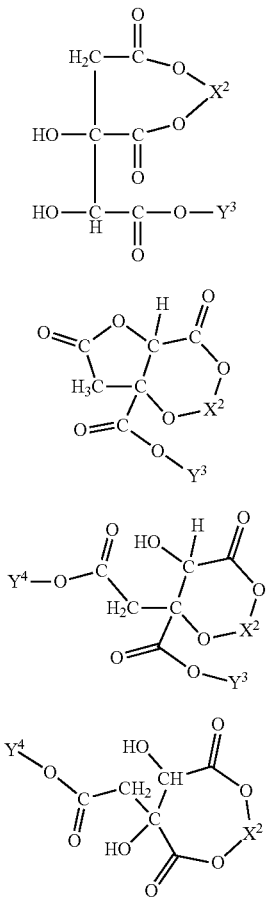

wherein:
- $X^2$ is a divalent metal selected from Group IIA metals, Group IIB metals, Mn, Tc and Re; and
- $Y^3$ and $Y^4$ are each independently hydrogen or a monovalent metal.

2. The composition of claim 1, wherein $Y^2$ is hydrogen or a monovalent metal.

3. The composition of claim 1, wherein the lactone form of the compound is the lactone of Formula (II):

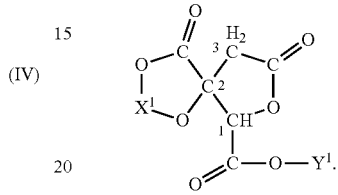

4. The composition of claim 1, wherein $X^1$ is a Group IIA group metal.

5. The composition of claim 1, wherein $X^1$ is a Group IIB group metal.

6. The composition of claim 1, wherein $X^1$ is a divalent metal selected from the group consisting of Mn, Tc and Re.

7. The composition of claim 1, wherein $Y^1$ and $Y^2$ are each independently a Group IA metal.

8. The composition of claim 1, wherein at least one of $Y^1$ and $Y^2$ is H.

9. The composition of claim 1, wherein the HCA is (−)-hydroxycitric acid.

10. The pharmaceutical or nutraceutical composition of claim 1, wherein the compound is a compound of any one of Tables 1-3.

* * * * *